US011246753B2

(12) United States Patent
Horvath et al.

(10) Patent No.: US 11,246,753 B2
(45) Date of Patent: Feb. 15, 2022

(54) MANUALLY ADJUSTABLE INTRAOCULAR FLOW REGULATION

(71) Applicant: AqueSys, Inc., Aliso Viejo, CA (US)

(72) Inventors: Christopher Horvath, Mission Viejo, CA (US); Laszlo O. Romoda, San Clemente, CA (US); Michael Robinson, Huntington Beach, CA (US)

(73) Assignee: AQUESYS, INC., Parsippany, NJ (US)

( * ) Notice: Subject to any disclaimer, the term of this patent is extended or adjusted under 35 U.S.C. 154(b) by 576 days.

(21) Appl. No.: 15/807,503

(22) Filed: Nov. 8, 2017

(65) Prior Publication Data

US 2019/0133826 A1 May 9, 2019

(51) Int. Cl.
*A61F 9/007* (2006.01)
(52) U.S. Cl.
CPC .. *A61F 9/00781* (2013.01); *A61F 2250/0013* (2013.01); *A61F 2250/0067* (2013.01); *A61F 2250/0069* (2013.01)
(58) Field of Classification Search
CPC .......... A61F 9/00781; A61F 2250/0013; A61F 2250/0069; A61F 2250/0067; A61F 2210/0004; A61B 3/16; A61B 5/076
See application file for complete search history.

(56) References Cited

U.S. PATENT DOCUMENTS

| 3,654,932 | A | * | 4/1972 | Newkirk | A61M 25/02 604/9 |
|---|---|---|---|---|---|
| 3,788,327 | A | | 1/1974 | Donowitz et al. | |
| 3,960,150 | A | | 6/1976 | Hussain et al. | |
| 4,090,530 | A | | 5/1978 | Lange | |
| 4,402,308 | A | | 9/1983 | Scott | |
| 4,562,463 | A | | 12/1985 | Lipton | |
| 4,583,117 | A | | 4/1986 | Lipton et al. | |
| 4,613,329 | A | | 9/1986 | Bodicky | |
| 4,700,692 | A | | 10/1987 | Baumgartner | |
| 4,722,724 | A | | 2/1988 | Schocket | |
| 4,730,613 | A | | 3/1988 | Gordy | |
| 4,744,362 | A | | 5/1988 | Grundler | |
| 4,750,901 | A | | 6/1988 | Molteno | |

(Continued)

FOREIGN PATENT DOCUMENTS

| CN | 1189780 | 8/1998 |
|---|---|---|
| CN | 1402625 | 3/2003 |

(Continued)

OTHER PUBLICATIONS

Coran, Pediatric Surgery, vol. e, 7 th edition, published on Feb. 14, 2012, pp. 1673-1697.

(Continued)

*Primary Examiner* — Nicholas J Weiss
*Assistant Examiner* — Alessandro R Del Priore
(74) *Attorney, Agent, or Firm* — Nathan S. Smith; Sujohn Das; Morgan, Lewis & Bockius LLP

(57) ABSTRACT

An implanted intraocular shunt can be manually manipulated, without surgical intervention, to modify the flow resistance of the shunt, thereby providing relief from high intraocular pressure while avoiding hypotony. For example, through application of pressure along a surface of the eye, a portion of the shunt can be displaced or separated relative to the shunt, thereby decreasing a flow resistance of the shunt.

19 Claims, 8 Drawing Sheets

(56) References Cited

U.S. PATENT DOCUMENTS

| | | |
|---|---|---|
| 4,787,885 A | 11/1988 | Binder |
| 4,804,382 A | 2/1989 | Turina et al. |
| 4,820,626 A | 4/1989 | Williams et al. |
| 4,826,478 A | 5/1989 | Schocket |
| 4,836,201 A | 6/1989 | Patton et al. |
| 4,848,340 A | 7/1989 | Bille et al. |
| 4,863,457 A | 9/1989 | Lee |
| 4,902,292 A | 2/1990 | Joseph |
| 4,908,024 A | 3/1990 | Py |
| 4,911,161 A | 3/1990 | Schechter |
| 4,915,684 A | 4/1990 | MacKeen et al. |
| 4,934,363 A | 6/1990 | Smith et al. |
| 4,936,825 A | 6/1990 | Ungerleider |
| 4,946,436 A | 8/1990 | Smith |
| 4,968,296 A | 11/1990 | Ritch et al. |
| 4,978,352 A | 12/1990 | Fedorov et al. |
| 5,041,081 A | 8/1991 | Odrich |
| 5,057,098 A | 10/1991 | Zelman |
| 5,071,408 A | 12/1991 | Ahmed |
| 5,092,837 A | 3/1992 | Ritch et al. |
| 5,098,426 A | 3/1992 | Sklar et al. |
| 5,098,443 A | 3/1992 | Parel et al. |
| 5,162,641 A | 11/1992 | Fountain |
| 5,167,645 A | 12/1992 | Castillo |
| 5,171,213 A * | 12/1992 | Price, Jr. ............ A61F 9/00781 604/294 |
| 5,178,604 A | 1/1993 | Baerveldt et al. |
| 5,180,362 A | 1/1993 | Worst |
| 5,201,750 A | 4/1993 | Hocherl et al. |
| 5,207,660 A | 5/1993 | Lincoff |
| 5,273,530 A | 12/1993 | Del Cerro |
| 5,275,622 A | 1/1994 | Lazarus et al. |
| 5,290,295 A | 3/1994 | Querals et al. |
| 5,300,020 A | 4/1994 | L'Esperance, Jr. |
| 5,333,619 A | 8/1994 | Burgio |
| 5,338,291 A | 8/1994 | Speckman et al. |
| 5,342,370 A | 8/1994 | Simon et al. |
| 5,351,678 A | 10/1994 | Clayton |
| 5,360,339 A | 11/1994 | Rosenberg |
| 5,368,015 A | 11/1994 | Wilk |
| 5,370,607 A | 12/1994 | Memmen |
| 5,399,951 A | 3/1995 | Lavallee et al. |
| 5,410,638 A | 4/1995 | Colgate et al. |
| 5,443,505 A | 8/1995 | Wong et al. |
| 5,472,439 A | 12/1995 | Hurd |
| 5,476,445 A | 12/1995 | Baerveldt et al. |
| 5,516,522 A | 5/1996 | Peyman et al. |
| 5,520,631 A | 5/1996 | Nordquist et al. |
| 5,558,629 A | 9/1996 | Baerveldt et al. |
| 5,558,630 A | 9/1996 | Fisher |
| 5,573,544 A | 11/1996 | Simon et al. |
| 5,601,094 A | 2/1997 | Reiss |
| 5,651,782 A | 7/1997 | Simon et al. |
| 5,656,026 A | 8/1997 | Joseph |
| 5,665,093 A | 9/1997 | Atkins et al. |
| 5,665,114 A | 9/1997 | Weadock et al. |
| 5,670,161 A | 9/1997 | Healy et al. |
| 5,676,679 A | 10/1997 | Simon et al. |
| 5,688,562 A | 11/1997 | Hsiung |
| 5,695,474 A | 12/1997 | Daugherty |
| 5,702,414 A | 12/1997 | Richter et al. |
| 5,704,907 A | 1/1998 | Nordquist et al. |
| 5,707,376 A | 1/1998 | Kavteladze et al. |
| 5,722,948 A | 3/1998 | Gross |
| 5,763,491 A | 6/1998 | Brandt et al. |
| 5,824,072 A | 10/1998 | Wong |
| 5,868,697 A | 2/1999 | Richter et al. |
| 5,908,449 A | 6/1999 | Bruchman et al. |
| 5,932,299 A | 8/1999 | Katoot |
| 5,938,583 A | 8/1999 | Grimm |
| 5,964,747 A | 10/1999 | Eaton et al. |
| 5,968,058 A | 10/1999 | Richter et al. |
| 6,007,511 A | 12/1999 | Prywes |
| 6,007,578 A | 12/1999 | Schachar |
| 6,050,970 A | 4/2000 | Baerveldt |
| 6,086,543 A | 7/2000 | Anderson et al. |
| 6,102,045 A | 8/2000 | Nordquist et al. |
| 6,146,366 A | 11/2000 | Schachar |
| 6,159,218 A | 12/2000 | Aramant et al. |
| 6,165,210 A | 12/2000 | Lau et al. |
| 6,203,513 B1 | 3/2001 | Yaron et al. |
| 6,228,023 B1 | 5/2001 | Zaslavsky et al. |
| 6,228,873 B1 | 5/2001 | Brandt et al. |
| 6,231,546 B1 | 5/2001 | Milo |
| 6,261,256 B1 | 7/2001 | Ahmed |
| 6,264,665 B1 | 7/2001 | Yu et al. |
| 6,280,468 B1 | 8/2001 | Schachar |
| 6,413,540 B1 | 7/2002 | Yaacobi |
| 6,450,937 B1 | 9/2002 | Mercereau et al. |
| 6,468,283 B1 | 10/2002 | Richter et al. |
| 6,471,666 B1 | 10/2002 | Odrich |
| 6,483,930 B1 | 11/2002 | Musgrave et al. |
| 6,510,600 B2 | 1/2003 | Yaron et al. |
| 6,514,238 B1 | 2/2003 | Hughes |
| 6,524,275 B1 | 2/2003 | Lynch et al. |
| 6,533,768 B1 | 3/2003 | Hill |
| 6,544,249 B1 | 4/2003 | Yu et al. |
| 6,558,342 B1 | 5/2003 | Yaron et al. |
| 6,595,945 B2 | 7/2003 | Brown |
| 6,638,239 B1 | 10/2003 | Bergheim et al. |
| 6,699,210 B2 | 3/2004 | Williams et al. |
| 6,726,664 B2 | 4/2004 | Yaron et al. |
| D490,152 S | 5/2004 | Myall et al. |
| 6,736,791 B1 | 5/2004 | Tu et al. |
| 6,752,753 B1 | 6/2004 | Hoskins et al. |
| 6,780,164 B2 | 8/2004 | Bergheim et al. |
| 6,881,198 B2 | 4/2005 | Brown |
| 6,899,717 B2 | 5/2005 | Weber et al. |
| 6,936,053 B1 | 8/2005 | Weiss |
| 6,939,298 B2 | 9/2005 | Brown et al. |
| 6,955,656 B2 | 10/2005 | Bergheim et al. |
| 7,008,396 B1 | 3/2006 | Straub |
| 7,037,335 B2 | 5/2006 | Freeman et al. |
| 7,041,077 B2 | 5/2006 | Shields |
| 7,094,225 B2 | 8/2006 | Tu et al. |
| 7,118,547 B2 | 10/2006 | Dahan |
| 7,135,009 B2 | 11/2006 | Tu et al. |
| 7,163,543 B2 | 1/2007 | Smedley et al. |
| 7,186,232 B1 | 3/2007 | Smedley et al. |
| 7,207,980 B2 | 4/2007 | Christian et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,709 B2 | 10/2008 | Pinchuk et al. |
| 7,431,710 B2 | 10/2008 | Tu et al. |
| 7,458,953 B2 | 12/2008 | Peyman |
| 7,481,816 B2 | 1/2009 | Richter et al. |
| 7,488,303 B1 | 2/2009 | Haffner et al. |
| 7,563,241 B2 | 7/2009 | Tu et al. |
| 7,594,899 B2 | 9/2009 | Pinchuk et al. |
| 7,625,384 B2 | 12/2009 | Eriksson et al. |
| 7,658,729 B2 | 2/2010 | Hull |
| 7,670,310 B2 | 3/2010 | Yaron et al. |
| 7,708,711 B2 | 5/2010 | Tu et al. |
| 7,722,549 B2 | 5/2010 | Nakao |
| 7,815,592 B2 | 10/2010 | Coroneo |
| 7,837,644 B2 | 11/2010 | Pinchuk et al. |
| 7,850,638 B2 | 12/2010 | Coroneo |
| 7,857,782 B2 | 12/2010 | Tu et al. |
| 7,867,186 B2 | 1/2011 | Haffner et al. |
| 7,867,205 B2 | 1/2011 | Bergheim et al. |
| 7,879,001 B2 | 2/2011 | Haffner et al. |
| 7,879,079 B2 | 2/2011 | Tu et al. |
| 7,892,282 B2 | 2/2011 | Shepherd |
| 7,951,155 B2 | 5/2011 | Smedley et al. |
| 8,007,459 B2 | 8/2011 | Haffner et al. |
| 8,062,244 B2 | 11/2011 | Tu et al. |
| 8,075,511 B2 | 12/2011 | Tu et al. |
| 8,109,896 B2 | 2/2012 | Nissan et al. |
| 8,118,768 B2 | 2/2012 | Tu et al. |
| 8,128,588 B2 | 3/2012 | Coroneo |
| 8,167,939 B2 | 5/2012 | Silvestrini et al. |
| 8,172,899 B2 | 5/2012 | Silvestrini et al. |

(56) References Cited

U.S. PATENT DOCUMENTS

| | | |
|---|---|---|
| 8,262,726 B2 | 9/2012 | Silvestrini et al. |
| 8,267,882 B2 | 9/2012 | Euteneuer et al. |
| 8,273,050 B2 | 9/2012 | Bergheim et al. |
| 8,277,437 B2 | 10/2012 | Saal et al. |
| 8,308,701 B2 | 11/2012 | Horvath et al. |
| 8,313,454 B2 | 11/2012 | Yaron et al. |
| 8,333,742 B2 | 12/2012 | Bergheim et al. |
| 8,337,393 B2 | 12/2012 | Silverstrini et al. |
| 8,337,445 B2 | 12/2012 | Tu et al. |
| 8,337,509 B2 | 12/2012 | Schieber et al. |
| 8,348,877 B2 | 1/2013 | Tu et al. |
| 8,377,122 B2 | 2/2013 | Silvestrini et al. |
| 8,425,449 B2 | 4/2013 | Wardle et al. |
| 8,444,589 B2 | 5/2013 | Silvestrini |
| 8,486,000 B2 | 7/2013 | Coroneo |
| 8,486,086 B2 | 7/2013 | Yaron et al. |
| 8,506,515 B2 | 8/2013 | Burns et al. |
| 8,512,404 B2 | 8/2013 | Frion et al. |
| 8,529,492 B2 | 9/2013 | Clauson et al. |
| 8,529,494 B2 | 9/2013 | Euteneuer et al. |
| 8,535,333 B2 | 9/2013 | de Juan, Jr et al. |
| 8,545,430 B2 | 10/2013 | Silvestrini |
| 8,551,166 B2 | 10/2013 | Schieber et al. |
| 8,574,294 B2 | 11/2013 | Silvestrini et al. |
| 8,579,846 B2 | 11/2013 | Tu et al. |
| 8,585,629 B2 | 11/2013 | Grabner et al. |
| 8,597,301 B2 | 12/2013 | Mitchell |
| 8,608,632 B1 | 12/2013 | Brigatti et al. |
| 8,663,303 B2 | 3/2014 | Horvath et al. |
| 8,721,702 B2 | 5/2014 | Romoda et al. |
| 8,758,290 B2 | 6/2014 | Horvath et al. |
| 8,765,210 B2 | 7/2014 | Romoda et al. |
| 8,801,766 B2 | 8/2014 | Reitsamer et al. |
| 8,828,070 B2 | 9/2014 | Romoda et al. |
| 8,852,136 B2 | 10/2014 | Horvath et al. |
| 8,852,137 B2 | 10/2014 | Horvath et al. |
| 8,852,256 B2 | 10/2014 | Horvath et al. |
| 8,974,511 B2 | 3/2015 | Horvath et al. |
| 9,017,276 B2 | 4/2015 | Horvath et al. |
| 9,044,301 B1 | 6/2015 | Pinchuk et al. |
| 9,095,411 B2 | 8/2015 | Horvath et al. |
| 9,095,413 B2 | 8/2015 | Romoda et al. |
| 9,192,516 B2 | 11/2015 | Horvath et al. |
| 9,271,869 B2 | 3/2016 | Horvath et al. |
| 9,283,116 B2 | 3/2016 | Romoda et al. |
| 9,326,891 B2 | 5/2016 | Horvath et al. |
| 9,393,153 B2 | 7/2016 | Horvath et al. |
| 10,828,196 B2 * | 11/2020 | Kahook ............... A61F 9/0008 |
| 2001/0025150 A1 | 9/2001 | de Juan et al. |
| 2001/0056254 A1 | 12/2001 | Cragg et al. |
| 2002/0026239 A1 | 2/2002 | Schachar |
| 2002/0087149 A1 | 7/2002 | McCary |
| 2002/0099434 A1 | 7/2002 | Buscemi et al. |
| 2002/0133168 A1 | 9/2002 | Smedley et al. |
| 2002/0177856 A1 | 11/2002 | Richter et al. |
| 2002/0193725 A1 | 12/2002 | Odrich |
| 2003/0015203 A1 | 1/2003 | Makower et al. |
| 2003/0050574 A1 | 3/2003 | Krueger |
| 2003/0060752 A1 | 3/2003 | Bergheim et al. |
| 2003/0079329 A1 | 5/2003 | Yaron et al. |
| 2003/0093084 A1 | 5/2003 | Nissan et al. |
| 2003/0097053 A1 | 5/2003 | Itoh |
| 2003/0181848 A1 | 9/2003 | Bergheim et al. |
| 2003/0187383 A1 | 10/2003 | Weber et al. |
| 2003/0187384 A1 | 10/2003 | Bergheim et al. |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 * | 2/2004 | Gharib ............... A61F 9/00781 604/8 |
| 2004/0054374 A1 | 3/2004 | Weber et al. |
| 2004/0073156 A1 | 4/2004 | Brown |
| 2004/0077987 A1 | 4/2004 | Rapacki et al. |
| 2004/0147870 A1 | 7/2004 | Burns et al. |
| 2004/0199130 A1 | 10/2004 | Chornenky et al. |
| 2004/0210185 A1 | 10/2004 | Tu et al. |
| 2004/0210209 A1 | 10/2004 | Yeung et al. |
| 2004/0215133 A1 | 10/2004 | Weber et al. |
| 2004/0216749 A1 | 11/2004 | Tu |
| 2004/0236343 A1 | 11/2004 | Taylor et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260227 A1 | 12/2004 | Lisk et al. |
| 2005/0049578 A1 | 3/2005 | Tu et al. |
| 2005/0101967 A1 | 5/2005 | Weber et al. |
| 2005/0119737 A1 | 6/2005 | Bene et al. |
| 2005/0143363 A1 | 6/2005 | De Juan et al. |
| 2005/0209549 A1 | 9/2005 | Bergheim et al. |
| 2005/0246023 A1 | 11/2005 | Yeung |
| 2005/0267398 A1 | 12/2005 | Protopsaltis et al. |
| 2005/0271704 A1 | 12/2005 | Tu et al. |
| 2005/0277864 A1 | 12/2005 | Haffner et al. |
| 2006/0052721 A1 | 3/2006 | Dunker et al. |
| 2006/0064112 A1 | 3/2006 | Perez |
| 2006/0074375 A1 | 4/2006 | Bergheim et al. |
| 2006/0084907 A1 | 4/2006 | Bergheim et al. |
| 2006/0106370 A1 | 5/2006 | Baerveldt et al. |
| 2006/0116605 A1 | 6/2006 | Nakao |
| 2006/0116625 A1 | 6/2006 | Renati et al. |
| 2006/0149194 A1 | 7/2006 | Conston et al. |
| 2006/0155238 A1 | 7/2006 | Shields |
| 2006/0155300 A1 | 7/2006 | Stamper et al. |
| 2006/0173397 A1 | 8/2006 | Tu et al. |
| 2006/0173446 A1 | 8/2006 | Dacquay et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0229633 A1 | 10/2006 | Shepherd |
| 2006/0241411 A1 | 10/2006 | Field et al. |
| 2006/0241749 A1 | 10/2006 | Tu et al. |
| 2007/0027537 A1 | 2/2007 | Castillejos |
| 2007/0093783 A1 | 4/2007 | Kugler et al. |
| 2007/0118065 A1 | 5/2007 | Pinchuk et al. |
| 2007/0141116 A1 | 6/2007 | Pinchuk et al. |
| 2007/0156079 A1 * | 7/2007 | Brown ............... A61B 3/16 604/9 |
| 2007/0172903 A1 | 7/2007 | Toner et al. |
| 2007/0191863 A1 | 8/2007 | De Juan et al. |
| 2007/0202186 A1 | 8/2007 | Yamamoto et al. |
| 2007/0263172 A1 | 11/2007 | Mura |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293872 A1 | 12/2007 | Peyman |
| 2008/0015633 A1 | 1/2008 | Abbott et al. |
| 2008/0027304 A1 | 1/2008 | Pardo et al. |
| 2008/0045878 A1 | 2/2008 | Bergheim et al. |
| 2008/0057106 A1 | 3/2008 | Erickson et al. |
| 2008/0108933 A1 | 5/2008 | Yu et al. |
| 2008/0147001 A1 | 6/2008 | Al-Marashi et al. |
| 2008/0181929 A1 | 7/2008 | Robinson et al. |
| 2008/0183121 A2 | 7/2008 | Smedley et al. |
| 2008/0249467 A1 | 10/2008 | Burnett et al. |
| 2008/0281277 A1 | 11/2008 | Thyzel |
| 2008/0312661 A1 | 12/2008 | Downer et al. |
| 2009/0036818 A1 | 2/2009 | Grahn et al. |
| 2009/0043321 A1 | 2/2009 | Conston et al. |
| 2009/0124973 A1 | 5/2009 | D'Agostino et al. |
| 2009/0137983 A1 | 5/2009 | Bergheim et al. |
| 2009/0138081 A1 | 5/2009 | Bergheim et al. |
| 2009/0182421 A1 | 7/2009 | Silvestrini et al. |
| 2009/0209910 A1 | 8/2009 | Kugler et al. |
| 2009/0216106 A1 | 8/2009 | Takii |
| 2009/0264813 A1 | 10/2009 | Chang |
| 2009/0270890 A1 | 10/2009 | Robinson et al. |
| 2009/0281520 A1 | 11/2009 | Highley et al. |
| 2009/0287136 A1 | 11/2009 | Castillejos |
| 2010/0004581 A1 | 1/2010 | Brigatti et al. |
| 2010/0010416 A1 | 1/2010 | Juan, Jr. et al. |
| 2010/0063478 A1 | 3/2010 | Selkee |
| 2010/0063512 A1 | 3/2010 | Braga |
| 2010/0098772 A1 | 4/2010 | Robinson et al. |
| 2010/0100104 A1 | 4/2010 | Yu et al. |

(56) References Cited

U.S. PATENT DOCUMENTS

| | | |
|---|---|---|
| 2010/0119696 A1 | 5/2010 | Yu et al. |
| 2010/0121248 A1 | 5/2010 | Yu et al. |
| 2010/0121249 A1 | 5/2010 | Yu et al. |
| 2010/0134759 A1 | 6/2010 | Silvestrini et al. |
| 2010/0137981 A1 | 6/2010 | Silvestrini et al. |
| 2010/0173866 A1 | 7/2010 | Hee et al. |
| 2010/0185138 A1 | 7/2010 | Yaron et al. |
| 2010/0191103 A1 | 7/2010 | Stamper et al. |
| 2010/0191224 A1 | 7/2010 | Butcher |
| 2010/0249691 A1 | 9/2010 | Van Der Mooren et al. |
| 2010/0274259 A1 | 10/2010 | Yaron et al. |
| 2010/0328606 A1 | 12/2010 | Peyman |
| 2011/0009874 A1 | 1/2011 | Wardle et al. |
| 2011/0028883 A1 | 2/2011 | Juan, Jr. et al. |
| 2011/0028884 A1 | 2/2011 | Coroneo |
| 2011/0046536 A1 | 2/2011 | Stegmann et al. |
| 2011/0087149 A1 | 4/2011 | Coroneo |
| 2011/0087150 A1 | 4/2011 | Coroneo |
| 2011/0087151 A1 | 4/2011 | Coroneo |
| 2011/0092878 A1 | 4/2011 | Tu et al. |
| 2011/0098627 A1 | 4/2011 | Wilcox |
| 2011/0098629 A1 | 4/2011 | Juan, Jr. et al. |
| 2011/0105987 A1 | 5/2011 | Bergheim et al. |
| 2011/0105990 A1 | 5/2011 | Silvestrini |
| 2011/0118745 A1 | 5/2011 | Yu et al. |
| 2011/0118835 A1 | 5/2011 | Silvestrini et al. |
| 2011/0230890 A1 | 9/2011 | Thyzel |
| 2011/0234976 A1 | 9/2011 | Kocaoglu et al. |
| 2011/0306915 A1 | 12/2011 | De Juan, Jr et al. |
| 2012/0078158 A1 | 3/2012 | Haffner et al. |
| 2012/0109040 A1 | 5/2012 | Smedley et al. |
| 2012/0123315 A1 | 5/2012 | Horvath et al. |
| 2012/0123316 A1 | 5/2012 | Horvath et al. |
| 2012/0123317 A1 | 5/2012 | Horvath et al. |
| 2012/0123430 A1 | 5/2012 | Horvath et al. |
| 2012/0123433 A1 | 5/2012 | Horvath et al. |
| 2012/0123434 A1 | 5/2012 | Grabner et al. |
| 2012/0123435 A1 | 5/2012 | Romoda et al. |
| 2012/0123436 A1 | 5/2012 | Reitsamer et al. |
| 2012/0123437 A1 | 5/2012 | Horvath et al. |
| 2012/0123438 A1 | 5/2012 | Horvath et al. |
| 2012/0123439 A1 | 5/2012 | Romoda et al. |
| 2012/0123440 A1 | 5/2012 | Horvath et al. |
| 2012/0165720 A1 | 6/2012 | Horvath et al. |
| 2012/0165721 A1 | 6/2012 | Grabner et al. |
| 2012/0165722 A1 | 6/2012 | Horvath et al. |
| 2012/0165723 A1 | 6/2012 | Horvath et al. |
| 2012/0165933 A1 | 6/2012 | Haffner et al. |
| 2012/0197175 A1 | 8/2012 | Horvath et al. |
| 2012/0220917 A1 | 8/2012 | Silvestrini et al. |
| 2012/0226150 A1 | 9/2012 | Balicki et al. |
| 2012/0253258 A1 | 10/2012 | Tu et al. |
| 2012/0310137 A1 | 12/2012 | Silvestrini |
| 2013/0006164 A1 | 1/2013 | Yaron et al. |
| 2013/0018295 A1 | 1/2013 | Haffner et al. |
| 2013/0018296 A1 | 1/2013 | Bergheim et al. |
| 2013/0110125 A1 | 5/2013 | Silvestrini et al. |
| 2013/0149429 A1 | 6/2013 | Romoda et al. |
| 2013/0150770 A1 | 6/2013 | Horvath et al. |
| 2013/0158462 A1 | 6/2013 | Wardle et al. |
| 2013/0184631 A1 | 7/2013 | Pinchuk |
| 2013/0211312 A1* | 8/2013 | Gelvin ............... A61F 9/00781 604/9 |
| 2013/0211314 A1* | 8/2013 | Venkatraman ...... A61F 9/00781 604/9 |
| 2013/0231603 A1 | 9/2013 | Wardle et al. |
| 2013/0237958 A1 | 9/2013 | Arrigo |
| 2013/0245532 A1 | 9/2013 | Tu |
| 2013/0245573 A1 | 9/2013 | de Juan, Jr et al. |
| 2013/0253404 A1 | 9/2013 | Tu |
| 2013/0253405 A1 | 9/2013 | Tu |
| 2013/0253406 A1 | 9/2013 | Horvath et al. |
| 2013/0253528 A1 | 9/2013 | Haffner et al. |
| 2013/0281817 A1 | 10/2013 | Schaller et al. |
| 2013/0281908 A1 | 10/2013 | Schaller et al. |
| 2013/0281910 A1 | 10/2013 | Tu |
| 2013/0310930 A1 | 11/2013 | Tu et al. |
| 2013/0345515 A1 | 12/2013 | Fitzmaaurice |
| 2014/0018720 A1 | 1/2014 | Horvath et al. |
| 2014/0066833 A1 | 3/2014 | Yaron et al. |
| 2014/0081195 A1 | 3/2014 | Clauson et al. |
| 2014/0135916 A1 | 5/2014 | Clauson et al. |
| 2014/0180189 A1 | 6/2014 | Horvath et al. |
| 2014/0213958 A1 | 7/2014 | Clauson et al. |
| 2014/0236065 A1 | 8/2014 | Romoda et al. |
| 2014/0236066 A1* | 8/2014 | Horvath ............... A61L 31/08 604/9 |
| 2014/0236067 A1 | 8/2014 | Horvath et al. |
| 2014/0243730 A1 | 8/2014 | Horvath |
| 2014/0272102 A1 | 9/2014 | Romoda et al. |
| 2014/0275923 A1 | 9/2014 | Haffner et al. |
| 2014/0276332 A1 | 9/2014 | Crimaldi et al. |
| 2014/0277349 A1 | 9/2014 | Vad |
| 2014/0287077 A1 | 9/2014 | Romoda et al. |
| 2014/0303544 A1 | 10/2014 | Haffner et al. |
| 2014/0323995 A1 | 10/2014 | Clauson et al. |
| 2014/0343476 A1 | 11/2014 | Penhasi |
| 2014/0371651 A1 | 12/2014 | Pinchuk |
| 2015/0005689 A1 | 1/2015 | Horvath et al. |
| 2015/0011926 A1 | 1/2015 | Reitsamer et al. |
| 2015/0038893 A1 | 2/2015 | Haffner et al. |
| 2015/0045714 A1 | 2/2015 | Horvath et al. |
| 2015/0057591 A1 | 2/2015 | Horvath et al. |
| 2015/0057597 A1* | 2/2015 | Johnson ............. A61F 9/00781 604/9 |
| 2015/0133946 A1 | 5/2015 | Horvath et al. |
| 2015/0238687 A1 | 8/2015 | Novakovic et al. |
| 2015/0265469 A1* | 9/2015 | Olson .................... A61M 1/84 604/8 |
| 2015/0290035 A1 | 10/2015 | Horvath et al. |
| 2015/0374545 A1 | 12/2015 | Horvath et al. |
| 2016/0135993 A1 | 5/2016 | Horvath et al. |
| 2016/0135994 A1 | 5/2016 | Romoda et al. |
| 2016/0158063 A1 | 6/2016 | Romoda et al. |
| 2016/0250071 A1 | 9/2016 | Horvath et al. |
| 2016/0256317 A1 | 9/2016 | Horvath et al. |
| 2016/0256318 A1 | 9/2016 | Horvath et al. |
| 2016/0256319 A1 | 9/2016 | Horvath et al. |
| 2016/0256320 A1 | 9/2016 | Horvath et al. |
| 2016/0256323 A1 | 9/2016 | Horvath et al. |
| 2016/0278982 A1 | 9/2016 | Horvath et al. |
| 2016/0354244 A1 | 12/2016 | Horvath et al. |
| 2016/0354245 A1 | 12/2016 | Horvath et al. |
| 2017/0087016 A1* | 3/2017 | Camras ............... A61F 9/00781 |
| 2017/0172797 A1 | 6/2017 | Horvath et al. |
| 2017/0172798 A1 | 6/2017 | Horvath et al. |
| 2017/0172799 A1 | 6/2017 | Horvath et al. |
| 2017/0348150 A1 | 12/2017 | Horvath et al. |
| 2018/0199797 A1 | 7/2018 | London |
| 2019/0030285 A1 | 1/2019 | Prabhu |
| 2019/0054272 A1 | 2/2019 | Tal |
| 2019/0069770 A1 | 3/2019 | Bourget |
| 2019/0290314 A1 | 9/2019 | Gemer |
| 2020/0046213 A1 | 2/2020 | Bendory |
| 2020/0054353 A1 | 2/2020 | Yun |

FOREIGN PATENT DOCUMENTS

| | | |
|---|---|---|
| CN | 1468090 | 1/2004 |
| CN | 1909859 | 2/2007 |
| CN | 101677823 | 3/2010 |
| CN | 102170840 | 8/2011 |
| CN | 102481171 | 5/2012 |
| CN | 102481171 A | 5/2012 |
| CN | 102510746 | 6/2012 |
| CN | 103284833 | 9/2013 |
| CN | 103313751 A | 9/2013 |
| GB | 2 296 663 A | 7/1996 |
| JP | 2009-523540 | 6/2009 |
| JP | 2009-542370 A | 12/2009 |
| JP | 2012-527318 | 11/2012 |
| JP | 2014-500758 | 1/2014 |
| JP | 2017-526504 | 9/2017 |
| RU | 2313315 C2 | 12/2007 |

(56) References Cited

FOREIGN PATENT DOCUMENTS

| | | |
|---|---|---|
| RU | 2482822 | 5/2013 |
| WO | WO-98/23237 A1 | 6/1998 |
| WO | WO-00/056255 A1 | 9/2000 |
| WO | WO-2002/74052 A2 | 9/2002 |
| WO | WO-2007/087061 A2 | 8/2007 |
| WO | WO-2008/005873 A2 | 1/2008 |
| WO | WO 2010/003011 | 1/2010 |
| WO | WO-2011/006078 A1 | 1/2011 |
| WO | WO 2011/155922 | 12/2011 |
| WO | WO 2012/040380 | 3/2012 |
| WO | WO-2012/068130 A1 | 5/2012 |
| WO | WO 2014/15 0292 | 9/2014 |
| WO | WO 2016/023942 | 2/2016 |
| WO | WO 2016/159999 | 10/2016 |
| WO | WO 2017/184881 | 10/2017 |

OTHER PUBLICATIONS

Quere, "Fluid Coating on a Fiber," Annu. Rev. Fluid Mech. 1999, 31:347-84.

Horvath, U.S. Appl. No. 15/703,802, "Intraocular Shunt Implantation," filed Sep. 13, 2017.

* cited by examiner

MANUALLY ADJUSTABLE INTRAOCULAR FLOW REGULATION

BACKGROUND

Glaucoma is a disease of the eye that affects millions of people. Glaucoma is associated with an increase in intraocular pressure resulting either from a failure of a drainage system of an eye to adequately remove aqueous humor from an anterior chamber of the eye or overproduction of aqueous humor by a ciliary body in the eye. Build-up of aqueous humor and resulting intraocular pressure may result in irreversible damage to the optic nerve and the retina, which may lead to irreversible retinal damage and blindness.

Glaucoma may be treated in a number of different ways. One manner of treatment involves delivery of drugs such as beta-blockers or prostaglandins to the eye to either reduce production of aqueous humor or increase flow of aqueous humor from an anterior chamber of the eye. Glaucoma filtration surgery is a surgical procedure typically used to treat glaucoma. The procedure involves placing a shunt in the eye to relieve intraocular pressure by creating a pathway for draining aqueous humor from the anterior chamber of the eye. The shunt is typically positioned in the eye such that it creates a drainage pathway between the anterior chamber of the eye and a region of lower pressure. Such fluid flow pathways allow for aqueous humor to exit the anterior chamber.

SUMMARY

The importance of lowering intraocular pressure (TOP) in delaying glaucomatous progression is well documented. When drug therapy fails, or is not tolerated, surgical intervention is warranted. There are various surgical filtration methods for lowering intraocular pressure by creating a fluid flow-path between the anterior chamber and the subconjunctival tissue. In one particular method, an intraocular shunt is implanted by directing a needle which holds the shunt through the cornea, across the anterior chamber, and through the trabecular meshwork and sclera, and into the subconjunctival space. See, for example, U.S. Pat. No. 6,544,249, U.S. Patent Publication No. 2008/0108933, and U.S. Pat. No. 6,007,511, the entireties of which are incorporated herein by reference.

However, existing implantable shunts may not always effectively regulate fluid flow from the anterior chamber. Fluid flow through a traditional shunt is passive, from the anterior chamber to a drainage structure of the eye. Further, in some circumstances, an implanted shunt may permit too much flow from the anterior chamber. If fluid flows from the anterior chamber at a rate greater than it can be produced in the anterior chamber, the surgery can result in an undesirably low intraocular pressure in the anterior chamber of the eye. This condition is known as hypotony. Hypotony occurs when the intraocular pressure is generally less than about 6 mmHg. Risks associated with low intraocular pressure and hypotony include blurred vision, collapse of the anterior chamber, and potentially significant damage to the eye. Such risks could require additional surgical intervention to repair. However, if fluid flow from the eye is not great enough, pressure in the anterior chamber will not be relieved, and damage to the optic nerve and the retina may still occur.

Accordingly, the present disclosure contemplates these issues and includes the realization that an intraocular shunt may be most effective if it can be adjusted or modified one or more times after implantation. Thus, some embodiments disclosed herein provide intraocular implants or shunts for draining fluid from an anterior chamber of an eye and methods of use that enable a clinician to remove a removable portion, such as an occlusion, to permit flow therethrough or to selectively adjust the flow rate, flow restriction, or other flow parameters of an intraocular shunt in order to avoid hypotony while ensuring that adequate pressure relief is provided. In some methods, a tool or other device, such as the clinician's finger, can be used to apply a force to an external surface of the eye to manually adjust or modify the shunt.

For example, after an intraocular shunt has been implanted in the eye, it will extend between an anterior chamber of the eye and a location of lower pressure of the eye. A clinician can determine a position of the shunt in the eye, for example, with or without the use of an imaging device or tool, such as gonioscope. Once the position of the shunt is determined, a force can be applied to an outer surface of the eye to modify structure of the shunt to remove a removable portion or to change a degree of flow restriction through the shunt.

The applied force can separate a removable portion from an outflow portion of the intraocular shunt. Before separation, the removable portion can occlude fluid flow through the intraocular shunt or alternatively, permit a degree of fluid flow through the shunt. After the removable portion is separated, the degree of flow restriction through the shunt will be reduced and an increased flow rate through the shunt will then be possible.

As noted above, a tool or other device, such as a finger, can be used to manually manipulate or apply a force to the shunt to manually adjust or modify one or more removable areas or portions of the shunt. The removable areas or portions of the shunt that can be modified by the application of force, such as compression, shear, and/or tension.

In some embodiments, the force applied to the eye can be a massaging motion. Further, in some embodiments, a clinician can use a finger to manually apply force to the outer surface of the eye. Alternatively, in some embodiments, the clinician can use a tool to apply force to the outer surface of the eye.

The removable portions can comprise discrete components of the shunt, such as a plug(s) and/or constricted tubular section(s) of the shunt. When present, these removable portions provide a partial or complete flow restriction that limits flow through the shunt. However, when the force is applied to the shunt, the removable portion can be at least partially or fully dislocated or separated from the remainder or body of the shunt, thereby removing, reducing, or initiating the lessening of the flow restriction.

For example, in some embodiments, the removable portion can have a first inner cross-sectional dimension and the body of the intraocular shunt can have a second inner cross-sectional dimension. The cross-sectional dimension of the body of the intraocular shunt can be greater than the cross-sectional dimension of the removable portion. In some embodiments, when force is applied, the cross-sectional dimension of the body of the intraocular shunt can be made smaller than the cross-sectional dimension of the removable portion.

In some embodiments, the removable portion can be at least partially positioned within the intraocular shunt. However, in some embodiments, the removable portion can be attached to an outer surface or end portion or surface of the shunt body. In some embodiments, when removable portion is removed, a flow rate through the intraocular shunt can increase from zero to a non-zero flow rate. Alternatively, when the removable portion is removed, the permitted flow rate can increase from a nonzero flow rate to a greater flow rate. Further, in some embodiments, after the removable portion is separated from the shunt, the removable portion can be spaced apart from the outflow portion of the shunt. Thereafter, in some embodiments, the removable portion can be extracted from the eye. However, in some embodiments, the removable portion can also be left in the eye to "tent" the outflow area around the outflow end portion of the shunt.

BRIEF DESCRIPTION OF THE DRAWINGS

The accompanying drawings, which are included to provide further understanding of the subject technology and are incorporated in and constitute a part of this specification, illustrate aspects of the disclosure and together with the description serve to explain the principles of the subject technology.

DETAILED DESCRIPTION

Figure 1:
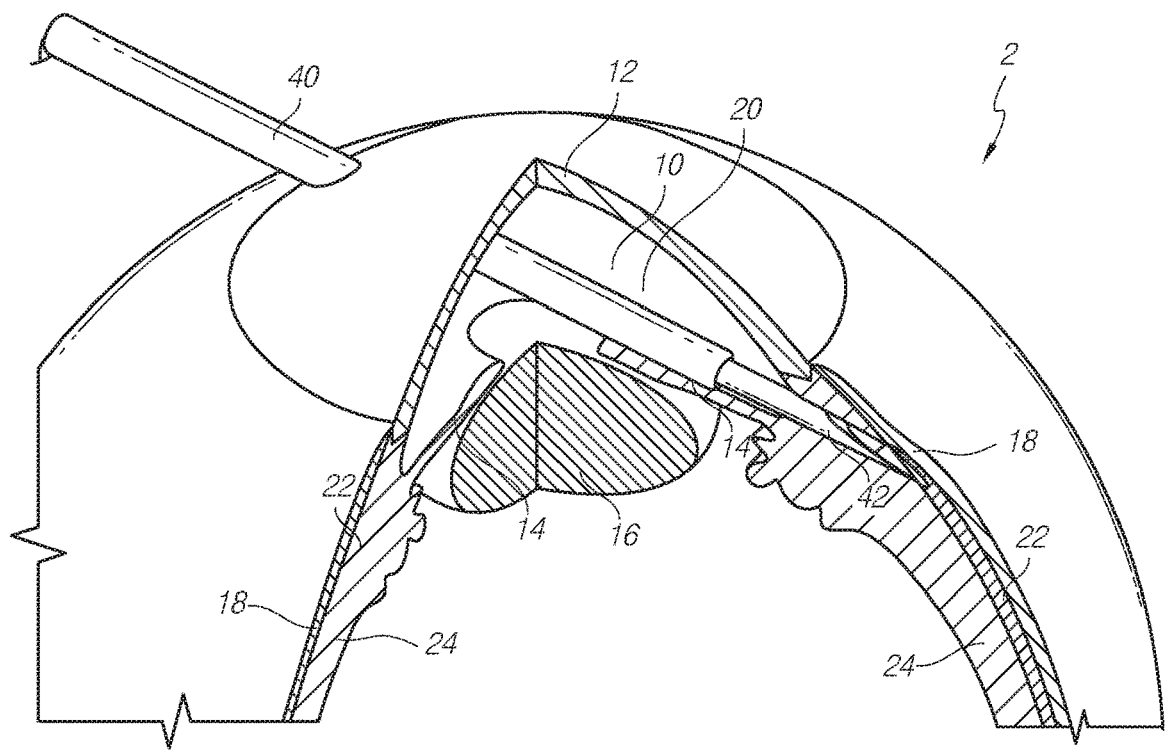
FIG. 1 is a partial cross-sectional diagram of an eye, illustrating ab interno insertion of a deployment device, according to some embodiments.

In the following detailed description, numerous specific details are set forth to provide a full understanding of the subject technology. It should be understood that the subject technology may be practiced without some of these specific details. In other instances, well-known structures and techniques have not been shown in detail so as not to obscure the subject technology.

As noted above, glaucoma filtration surgery can often result in an undesirably low intraocular pressure in the anterior chamber of the eye and can often lead to hypotony. The present disclosure provides various embodiments of methods and devices that can enable a clinician to generally prevent hypotony after a glaucoma filtration surgery while enabling the clinician to ensure adequate pressure relief by adjusting the flow through an intraocular shunt. As used herein, the term "shunt" includes hollow microfistula tubes similar to the type generally described in U.S. Pat. No. 6,544,249 as well as other structures that include one or more lumens or other flow paths therethrough.

An aspect of some embodiments is the realization that there are various unpredictable factors related to the success of a surgical intervention. Fundamentally, a successful surgical intervention relieves intraocular pressure without causing hypotony. In order to be successful, the flow through a shunt and the resulting intraocular pressure in the anterior chamber must account for various unpredictable biological factors, such as aqueous production amount, viscosity of the aqueous humor, and other biological outflow restrictions.

The biological outflow restrictions associated with a shunt depend on the overall outflow resistance or restrictions of the targeted space where the shunt is placed. The biological outflow restrictions of the subconjuctval space, for example, depend on: (1) the strength and amount and thickness of the tenon adhesions, if present (e.g., placed ab interno); (2) the thickness and consistency of conjunctiva, which can allow more or less fluid to diffuse into the sub-conjuctval vessels and into the tear film; (3) existing fibrotic adhesions; (4) the presence of lymphatic outflow pathways (some pathways may already exist at the time of shunt placement, but often the lymphatic pathways can be created and increase days and weeks after the flow has started); (5) the amount of diffusion into episcleral vessels; (6) the amount of fibrosis build-up after implant placement (which can be triggered by aqueous humor, start forming in the first one to four weeks after surgery, and can lead to a significant or total outflow restriction). Most of these factors vary greatly patient by patient and are for the most part currently unpredictable. The potential fibrotic response is the biggest changing factor in biological outflow resistance and can range from no significant outflow restriction over the first three months post-op to a total flow blockage within one week after surgery.

These patient variations and their dynamic nature post-operatively make it very difficult to maintain an optimal intraocular pressure with a "static" shunt placement. A "static" shunt placement can be referred to as a procedure or surgery in which a shunt is implanted and maintained without any change to its own flow resistance parameters or shunt outflow resistance, such as length, lumen diameter, or other features that would affect the flow rate through the shunt. Thus, excluding biological flow resistance changes in the target space, such as those mentioned immediately above, a "static" shunt or "static" shunt placement will not result in variations to the flow parameters or shunt outflow resistance of the shunt.

A static shunt usually provides substantial outflow in the early post-op phase (one day to two weeks) due to the absence of fibrotic tissue (or other biological outflow restrictions) early on. This can often lead to a less than desirable intraocular pressure in the anterior chamber for this early phase, often hypotony, and an increased risk for complications associated with such low intraocular pressures. Then, after the initial phase (e.g., after a few days to a few weeks), some patients experience a strong fibrotic response that can create high biological outflow restrictions that can result in a higher than desired intraocular pressure (e.g., above 20 mmHg).

Some embodiments disclosed herein provide a manner to overcome these complications and uncertainties of traditional surgery. For example, a flow-tunable shunt can be provided that can be manually modified or self-adjusted after the surgery without surgical intervention in order to maintain an optimal outflow resistance that can compensate for an increase in biological outflow resistance. Indeed, although methods and devices have been disclosed that permit additional intervention to modify a shunt's flow resistance after the shunt has been implanted, such as that disclosed in Applicant's own U.S. Publication No. 2014/

0236066, filed on Feb. 19, 2013, U.S. Publication No. 2016/0354244, filed on Jun. 2, 2016, and U.S. Publication No. 2016/0354245, filed on Jun. 2, 2016, the entirety of each of which is incorporated herein by reference, the present disclosure provides methods and devices that permit a clinician to quickly evaluate and modify a shunt without surgical intervention. The entire procedure may be performed with or without topical anesthesia and may be done in an outpatient setting, thus providing a simple procedure, reduced costs, low latency, and low recovery time for the patient.

As used herein, a "nonsurgical intervention" is considered to be one in which the patient's eye is not cut or pierced. This nonsurgical intervention can allow a clinician to monitor and maintain an optimal intraocular pressure throughout changing tissue stages (e.g., changes in the biological outflow restriction of the targeted space, such as those mentioned above) that usually increase the biological outflow resistance and lead to higher intraocular pressures. Further, such procedures provide distinct advantages over conventional interventions that often require substantial, invasive procedures and lengthy healing by the patient.

Therefore, in some embodiments, shunt devices and methods of use can provide substantial initial outflow resistance in order to avoid early low post-op intraocular pressures and hypotony and control over subsequent lessening of outflow resistance to compensate for a rising biological outflow resistance (e.g., fibrosis of the targeted space). The shunt can be configured such that the flow resistance is manually or surgically tuned by the clinician or specifically configured to self-adjust (e.g., through the use of dissolvable sections) over time.

Various structures and/or regions of the eye having lower pressure that have been targeted for aqueous humor drainage include Schlemm's canal, the subconjunctival space, the episcleral vein, the suprachoroidal space, the intra-Tenon's adhesion space, and the subarachnoid space. Shunts may be implanted using an ab externo approach (e.g., entering through the conjunctiva and inwards through the sclera) or an ab interno approach (e.g., entering through the cornea, across the anterior chamber, through the trabecular meshwork and sclera). For example, ab interno approaches for implanting an intraocular shunt in the subconjunctival space are shown for example in Yu et al. (U.S. Pat. No. 6,544,249 and U.S. Patent Publication No. 2008/0108933) and Prywes (U.S. Pat. No. 6,007,511), the contents of each of which are incorporated by reference herein in its entirety.

Some methods can involve inserting into the eye a hollow shaft configured to hold an intraocular shunt. In some embodiments, the hollow shaft can be a component of a deployment device that may deploy the intraocular shunt. The hollow shaft can be coupled to a deployment device or be part of the deployment device itself. Deployment devices that are suitable for deploying shunts according to the invention include, but are not limited to the deployment devices described in U.S. Pat. Nos. 6,007,511, 6,544,249, and U.S. Publication No. 2008/0108933, the contents of each of which are incorporated herein by reference in their entireties. The deployment devices can include devices such as those as described in co-pending and co-owned U.S. Publication No. 2012/0123434, filed on Nov. 15, 2010, U.S. Publication No. 2012/0123439, filed on Nov. 15, 2010, and co-pending U.S. Publication No. 2013/0150770, filed on Dec. 8, 2011, the contents of each of which are incorporated by reference herein in their entireties.

The shunt can be deployed from the shaft into the eye such that the shunt forms a passage from the anterior chamber into an area of lower pressure, such as Schlemm's canal, the subconjunctival space, the episcleral vein, the suprachoroidal space, the intra-Tenon's adhesion space, the subarachnoid space, or other areas of the eye. The hollow shaft is then withdrawn from the eye. Methods for delivering and implanting bioabsorbable or permanent tubes or shunts, as well as implantation devices for performing such methods, are generally disclosed in applicant's co-pending applications, U.S. Publication No. 2013/0150770, filed on Dec. 8, 2011, and U.S. Publication No. 2012/0197175, filed on Dec. 8, 2011, as well as in U.S. Pat. Nos. 6,544,249 and 6,007,511, each of which are incorporated by reference in their entireties. Embodiments of the shunts disclosed herein can be implanted using such methods and others as discussed herein.

Some methods can be conducted by making an incision in the eye prior to insertion of the deployment device. However, in some instances, the method may be conducted without making an incision in the eye prior to insertion of the deployment device. In some embodiments, the shaft that is connected to the deployment device has a sharpened point or tip. In some embodiments, the hollow shaft is a needle. Exemplary needles that may be used are commercially available from Terumo Medical Corp. (Elkington, Md.). In some embodiments, the needle can have a hollow interior and a beveled tip, and the intraocular shunt can be held within the hollow interior of the needle. In some embodiments, the needle can have a hollow interior and a triple ground point or tip.

Some methods can be conducted without needing to remove an anatomical portion or feature of the eye, including but not limited to the trabecular meshwork, the iris, the cornea, or aqueous humor. Some methods can be conducted without inducing substantial ocular inflammation, such as subconjunctival blebbing or endophthalmitis. Some methods can be achieved using an ab interno approach by inserting the hollow shaft configured to hold the intraocular shunt through the cornea, across the anterior chamber, through the trabecular meshwork, and into the intra-scleral or intra-Tenon's adhesion space. However, some methods may be conducted using an ab externo approach.

In some methods conducted using an ab interno approach, the angle of entry through the cornea can be altered to affect optimal placement of the shunt in the intra-Tenon's adhesion space. The hollow shaft can be inserted into the eye at an angle above or below the corneal limbus, in contrast with entering through the corneal limbus. For example, the hollow shaft can be inserted from about 0.25 mm to about 3.0 mm above the corneal limbus. The shaft can be inserted from about 0.5 mm to about 2.5 mm above the corneal limbus. The shaft can also be inserted from about 1.0 mm to about 2.0 mm above the corneal limbus, or any specific value within any of these ranges. For example, the hollow shaft can be inserted above the corneal limbus at distances of about: 1.0 mm, 1.1 mm, 1.2 mm, 1.3 mm, 1.4 mm, 1.5 mm, 1.6 mm, 1.7 mm, 1.8 mm, 1.9 mm, or 2.0 mm.

Further, in some embodiments, placement of the shunt farther from the limbus at the exit site, as provided by an angle of entry above the limbus, can provide access to more lymphatic channels for drainage of aqueous humor, such as the episcleral lymphatic network, in addition to the conjunctival lymphatic system. A higher angle of entry also results in flatter placement in the intra-Tenon's adhesion space so that there is less bending of the shunt.

As discussed in Applicant's co-pending application, U.S. Publication No. 2013/0150770, filed on Dec. 8, 2011, the entirety of which is incorporated herein by reference, in some embodiments, to ensure proper positioning and functioning of the intraocular shunt, the depth of penetration into the intra-Tenon's adhesion space may be important when performing some methods.

In some methods, the distal tip of the hollow shaft can pierce the sclera and intra-Tenon's adhesion space without coring, removing or causing major tissue distortion of the surrounding eye tissue. The shunt is then deployed from the shaft. Preferably, a distal portion of the hollow shaft (as opposed to the distal tip) completely enters the intra-Tenon's adhesion space before the shunt is deployed from the hollow shaft.

In accordance with some embodiments, the hollow shaft can comprise a flat bevel needle, such as a needle having a triple-ground point. The tip bevel can first pierce through the sclera and into the intra-Tenon's adhesion space by making a horizontal slit. In some methods, the needle can be advanced even further such that the entire flat bevel penetrates into the intra-Tenon's adhesion space, to spread and open the tissue to a full circular diameter.

Further, in accordance with an aspect of some methods, the intra-Tenon's channel can be urged open by the flat bevel portion of the needle so that the material around the opening is sufficiently stretched and a pinching of the shunt in that zone is avoided, thus preventing the shunt from failing due to the pinching or constriction. Full entry of the flat bevel into the intra-Tenon's adhesion space causes minor distortion and trauma to the local area. However, this area ultimately surrounds and conforms to the shunt once the shunt is deployed in the eye.

With reference to the figures, FIG. 1 is a schematic diagram that illustrates a manner of accessing the eye and delivering an intraocular shunt for treatment of glaucoma. As noted, some methods disclosed herein provide for an ab interno approach. As also noted, the ab interno approach may not be needed in order to perform the procedures or methods disclosed herein. For example, the shunt can be delivered using an ab externo approach, as discussed herein.

FIG. 1 illustrates the general anatomy of an eye 2. As illustrated, an anterior aspect of the anterior chamber 10 of the eye 2 is the cornea 12, and a posterior aspect of the anterior chamber 10 of the eye 2 is the iris 14. Beneath the iris 14 is the lens 16. The conjunctiva 18 is a thin transparent tissue that covers an outer surface of the eye 2. The anterior chamber 10 is filled with aqueous humor 20. The aqueous humor 20 drains into a space(s) 22 below the conjunctiva 18 through the trabecular meshwork (not shown in detail) of the sclera 24. The aqueous humor 20 is drained from the space(s) 22 below the conjunctiva 18 through a venous drainage system (not shown).

FIG. 1 illustrates a surgical intervention to implant an intraocular shunt into the eye using a delivery device 40 that holds the shunt, and deploying the shunt within the eye 2. FIG. 1 illustrates an ab interno approach in which the delivery device 40 has been inserted through the cornea 12 into the anterior chamber 10. As noted above, however, the implant can also be placed using an ab externo approach, in which the conjunctiva or Tenon's capsule can be dissected and pulled back, prior to placement of a shunt.

Referring to FIG. 1, the delivery device 40 can be advanced across the anterior chamber 10 in what is referred to as a transpupil implant insertion. The delivery device can be inserted through the anterior angle and advanced through the sclera 24 until accessing a targeted space, such as Schlemm's canal, the subconjunctival space, the episcleral vein, the suprachoroidal space, the intra-Tenon's adhesion space, the subarachnoid space, or other areas, as desired. The shunt is then deployed from the deployment device, producing a conduit between the anterior chamber and the targeted space to allow aqueous humor to drain through the traditional drainage channels of the eye, such as the intrascleral vein, the collector channel, Schlemm's canal, the trabecular outflow, the uveoscleral outflow to the ciliary muscle, the conjunctival lymphatic system, or others.

In some embodiments, the delivery device 40 can comprise a hollow shaft 42 that is configured to hold an intraocular shunt. The shaft may hold the shunt within the hollow interior of the shaft. Alternatively, the hollow shaft may hold the shunt on an outer surface of the shaft.

Figure 2:
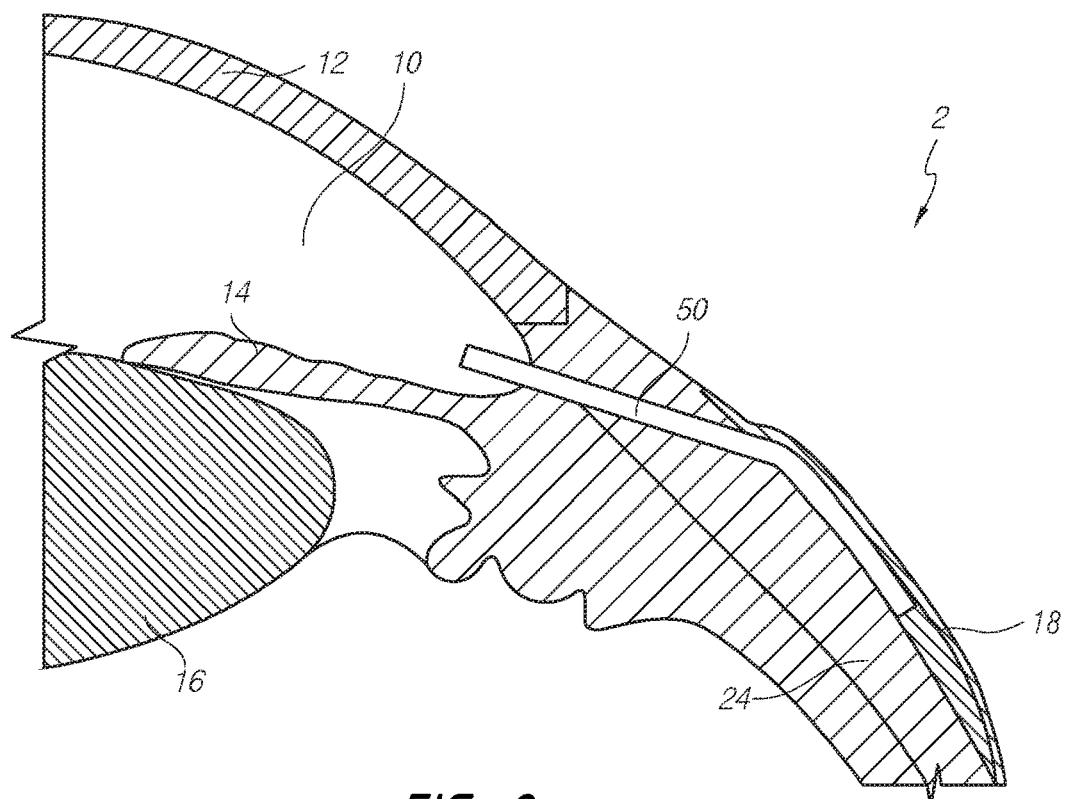
FIG. 2 illustrates a schematic placement of an intraocular shunt within intra-Tenon's adhesion space, according to some embodiments.

FIG. 2 provides a cross-sectional view of a portion of the eye 2, and provides greater detail regarding certain anatomical structures of the eye and placement of an intraocular shunt 50. In particular, FIG. 2 shows the shunt 50 implanted in the intra-Tenon's adhesion space between the conjunctiva 18 and the sclera 24. In some embodiments, intra-Tenon's placement can be achieved by not dissecting the conjunctiva, by controlling the scleral exit location, and by pretreatment of the intra-Tenon's adhesion space before or by tenon manipulation during the procedure. Placement of shunt 50 within the intra-Tenon's adhesion space allows aqueous humor 20 to diffuse into the subconjunctival space. According to some embodiments, the outflow restrictions of the subconjunctival space can depend on the strength, amount, and thickness of the tenon adhesions (if present, e.g., when placed ab interno), the thickness and consistency of the conjunctiva (which can allow more or less fluid to diffuse into the subconjunctival vessels and tear space), and existing fibrotic adhesions.

FIG. 2 illustrates one of a variety of potential placements of the shunt 50 in the eye. As discussed herein, methods and devices provided herein can be implemented wherein a shunt is placed in communication with other anatomical features of the eye. Thus, some methods and devices disclosed herein can be implemented when a shunt forms a passage from the anterior chamber into an area of lower pressure, such as Schlemm's canal, the subconjunctival space, the episcleral vein, the suprachoroidal space, the intra-Tenon's adhesion space, the subarachnoid space, or other areas of the eye.

The methods of implantation may be fully automated, partially automated (and thus, partially manual), or completely manual. For example, in a fully automated procedure, a shunt may be delivered by robotic implantation whereby a clinician controls the advancement of the needle, plunger, optional guidewire and, as a result, shunt by remotely controlling a robot. In such fully automated, remotely controlled procedures, the clinician's hands typically do not contact implantation apparatus during the surgical procedure. Alternatively, shunt may be delivered to the desired area of the eye with a "handheld" implantation apparatus. Handheld implantation devices, as well as details regarding steps and procedures of implantation methods, are described in co-pending U.S. Application Publication Nos. 2012/0197175, filed on Dec. 8, 2011, and 2013/0150770, filed on Dec. 8, 2011, the entireties of each of which are incorporated herein by reference. Insertion of the needle into the eye as well as certain repositioning or adjusting steps may be performed manually by the clinician. In the case of fully manual devices and methods, all of the positioning, repositioning, adjusting and implantation steps can be performed manually by the clinician.

Some embodiments disclosed herein comprise intraocular shunts that are configured to form a drainage pathway from the anterior chamber of the eye to a targeted space. In this manner, the shunt can allow aqueous humor to drain from the anterior chamber and out through the traditional drainage channels of the eye, such as the intra-scleral vein, the collector channel, Schlemm's canal, the trabecular outflow, the uveoscleral outflow to the ciliary muscle, the conjunctival lymphatic system, or others.

Some embodiments disclosed herein comprise a shunt that is generally cylindrically shaped with an outside cylindrical wall and, in some embodiments, a hollow interior that extends at least partially along the length of the shunt. The shunt can have a wall defining a main section inner diameter, lumen dimension, diameter, or a flow path cross-sectional dimension or diameter of from about 10 μm to about 300 μm. The shunt can have a wall defining a lumen dimension or diameter of from about 20 μm to about 200 μm. Further, the shunt can have a wall defining a lumen dimension or diameter of from about 30 μm to about 100 μm. In some embodiments, the shunt can have a wall defining a lumen dimension or diameter of about 50 μm.

As noted above, the restrictive section can provide a complete occlusion of the inner lumen of the shunt. In some embodiments, the restrictive section can also comprise a lumen or passage having an inner diameter. For example, the inner diameter of the restrictive section can be from about 10 μm to about 70 μm. In some embodiments, the restrictive section inner diameter can be from about 15 μm to about 35 μm. In some embodiments, the restrictive section inner diameter can be about 20 μm. Further, in some embodiments, the inner diameter of the shunt can remain the same, increase, or decrease when hydrated.

The outside dimension or diameter of the wall of some embodiments can be from about 100 μm to about 300 μm, from about 125 μm to about 250 μm, from about 140 μm to about 180 μm, or about 160 μm. Further, the wall thickness of some embodiments can be from about 30 μm to about 80 μm, from about 40 μm to about 50 μm, or about 45 μm. Further, in some embodiments, the outer diameter of the shunt can increase when hydrated.

In some embodiments, the intraocular shunt can have a length that is sufficient to form a drainage pathway from the anterior chamber of the eye to the targeted space. The length of the shunt is important for achieving placement specifically in the targeted space. A shunt that is too long will extend beyond the targeted space and may irritate the eye. For example, if the targeted space is the intra-scleral space, a shunt that is too long can irritate the conjunctiva which can cause the filtration procedure to fail. Further, in such embodiments, a shunt that is too short will not provide sufficient access to drainage pathways such as the episcleral lymphatic system or the conjunctival lymphatic system.

In some embodiments, the shunt may be any length that allows for drainage of aqueous humor from an anterior chamber of an eye to the targeted space. In some embodiments, the shunt can have a total length in the range of from about 1 mm to about 12 mm, whether in a dry or fully hydrated state. The length can be in the range of from about 2 mm to about 10 mm or from about 4 mm to about 8 mm, or any specific value within said ranges. In some embodiments, the length of the shunt is from about 5 mm to about 8 mm, or any specific value within this range, for example, such as about: 5.0 mm, 5.1 mm, 5.2 mm, 5.3 mm, 5.4 mm, 5.5 mm, 5.5 mm, 5.7 mm, 5.8 mm, 5.9 mm, 6.0 mm, 6.1 mm, 6.2 mm, 6.3 mm, 6.4 mm, 6.5 mm, 6.6 mm, 6.7 mm, 6.8 mm, 6.9 mm, 7 mm, 7.1 mm, 7.2 mm, 7.3 mm, 7.4 mm, 7.5 mm, 7.6 mm, 7.7 mm, 7.8 mm. 7.9 mm, or 8.0 mm. Further, in some embodiments, the length of the shunt can remain the same or increase when hydrated. For example, the length of the shunt can increase from about 5 mm when dry, swelling to a length of about 6 mm when fully hydrated.

Of the total shunt length, the axial length of the restrictive section can be from about 0.1 mm to about 6 mm. In some embodiments, the restrictive section length can be from about 0.5 mm to about 4 mm. In some embodiments, the restrictive section length can be about 2 mm.

Additionally, some embodiments of the shunt can have different shapes and different dimensions that may be accommodated by the eye. In accordance with embodiments disclosed herein, the intraocular shunt can be formed having dimensions within the various ranges of dimensions disclosed for outer diameter (e.g., of the main section or restrictive section), inner diameter (e.g., of the main section or restrictive section), segment lengths (e.g., of the restrictive section or main section), and total length.

For example, some embodiments can be configured such that the shunt has a total length of about 6 mm, a main section inner diameter of about 150 μm, and a restrictive section inner diameter of from about 40 μm to about 63 μm.

The Figures illustrate embodiments of an intraocular implant or shunt that can have a first flow that can be modified to a second flow by changing the configuration of the implant without requiring surgical intervention.

Some implants can be configured to have a first flow that can be changed to a second flow by dislodging, separating, or removing a removable portion of the restrictive section thereof. In some embodiments, the first flow can be less than the second flow through the implant. Thus, modification or removal of a section thereof can decrease the flow resistance through the implant and thereby permit increased flow through the implant.

For example, the Figures illustrate embodiments and configurations of flow-tunable implants or shunts having one or more partially obstructive or flow-limiting restrictive sections and one or more unobstructive or unrestrictive main sections.

Some embodiments of the shunts disclosed herein can provide a desired initial flow resistance or flow value that prevents excessive outflow from the anterior chamber of the eye, thus avoiding low intraocular pressures or hypotony. However, upon development of biological outflow resistance, a clinician can tune the flow resistance or flow value of the shunt to prevent high intraocular pressure. Accordingly, some embodiments herein enable a clinician to adjust or tune the flow rate of the shunt. The geometric configuration and dimensions of components of these shunts can be manipulated as desired to provide a desired flow resistance. Accordingly, the embodiments illustrated and discussed do not limit the scope of the features or teachings herein.

In accordance with some embodiments, the shunt can be configured such that the clinician can adjust the flow resistance or flow value to provide a flow rate of from about 1 μL per minute to about 3 μL per minute. Further, the shunt can be configured such that the clinician can adjust the flow resistance or flow value to provide a flow rate of about 2 μL per minute.

Figure 3:
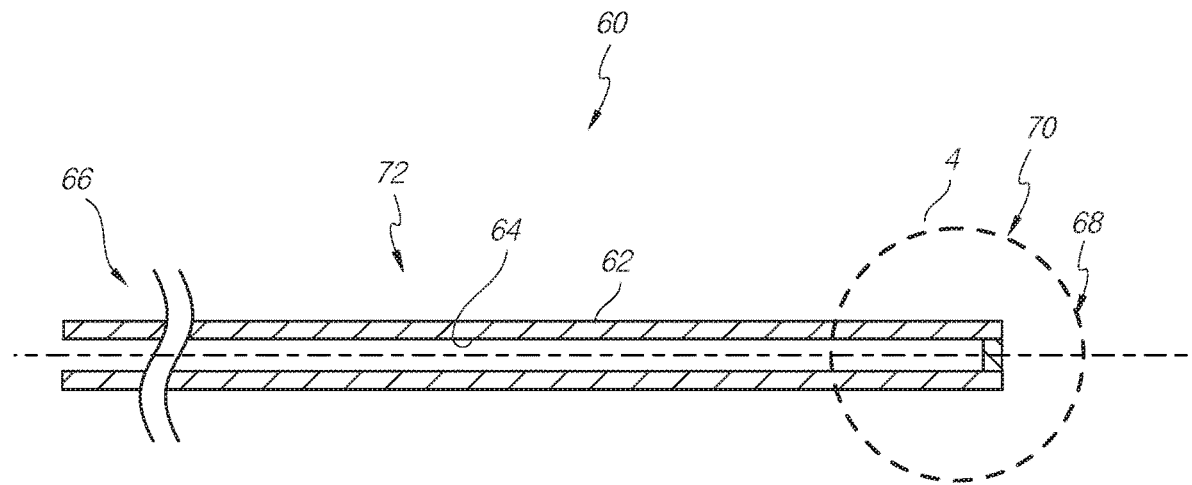
FIGS. 3 and 4 illustrate cross-sectional views of an intraocular shunt having a removable portion, according to some embodiments.
Figure 4:
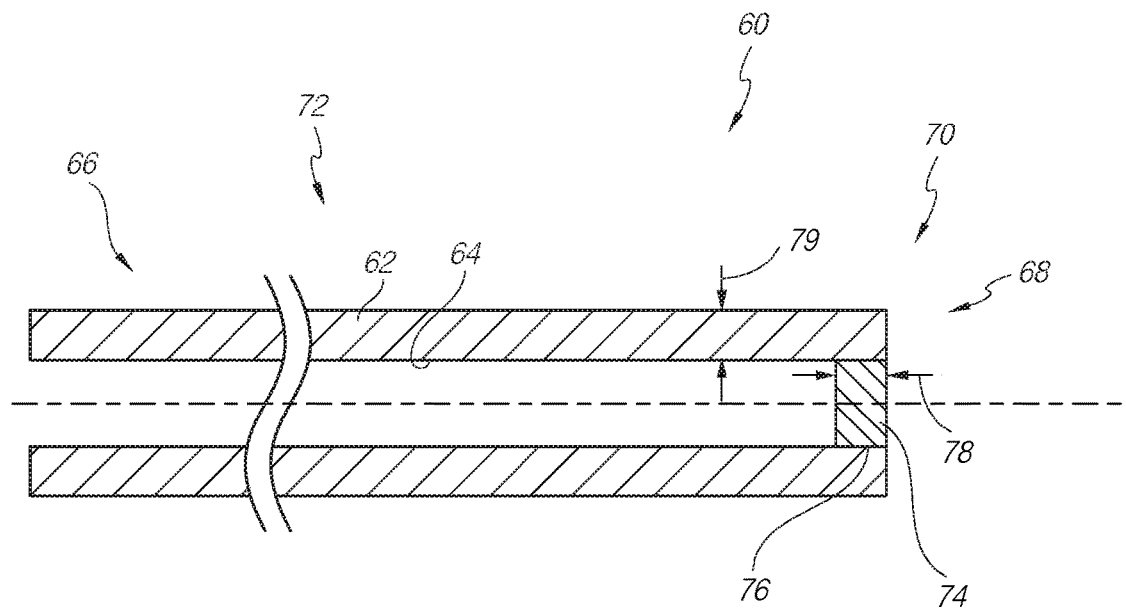
Figure 5:
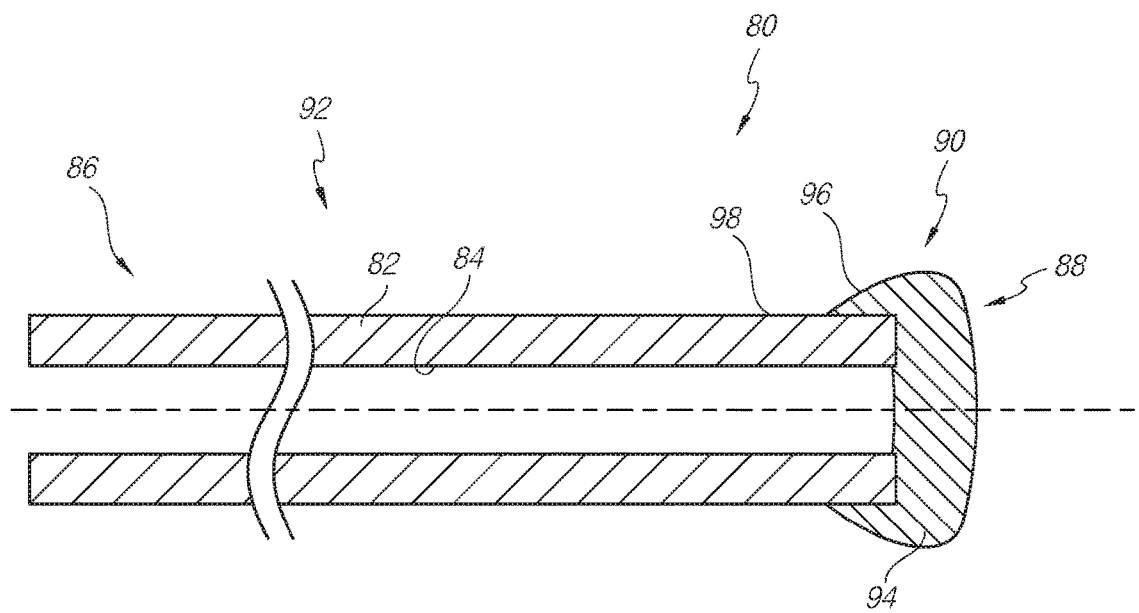
FIGS. 5-9 illustrate cross-sectional views of other intraocular shunts having a removable portion, according to some embodiments.

FIGS. 3-5 illustrate embodiments of intraocular shunts in which a removable portion provides a complete or total occlusion of fluid flow through the shunt. FIGS. 3 and 4 illustrate an embodiment in which the removable portion is positioned within a lumen of the shunt, while FIG. 5 illustrates an embodiment in which the removable portion is positioned around an outflow end portion of the shunt. In accordance with some embodiments, the flow occlusion can be a separate component or material that is inserted into the lumen, attached to the outflow end portion, or otherwise coated onto the outflow end portion of the shunt to block flow through the lumen. Thus, in some embodiments, FIGS. 3-5 illustrate shunts in which the flow through the shunt is initially blocked while FIGS. 6-9 illustrate shunts in which the flow through the shunt is reduced, but not blocked or completely closed so as to not permit flow therethrough.

With reference to FIG. 3, an intraocular shunt 60 can comprise an elongate body having a wall 62 that defines a shunt lumen 64 extending therethrough. The shunt 60 can comprise opposing end portions (e.g., an inlet end portion 66 and an outflow end portion 68). The inlet end portion 66 can be clear and permit flow thereinto, and the outflow end portion 68 can comprise one or more restrictions. The shunt 60 can comprise an obstructive or flow-limiting restrictive section 70 and an unobstructive or unrestrictive main section 72. The shunt lumen 64 can extend through the main section 72. In the illustrated embodiment, flow through the restrictive section 70 is occluded or blocked.

FIG. 4 illustrates the restrictive section 70 of the shunt 60 in greater detail. The restrictive section 70 can comprise a flow restrictor, removable portion, or plug 74 that is positioned within the lumen 64 at the outflow end portion 68 of the shunt 60. The plug 74 can comprise a generally circular disk or cylinder that is inserted into the lumen 64. The plug 74 can provide a burstable seal across the outflow end portion 68.

The plug 74 can comprise an axial thickness (measured along the longitudinal axis) that allows the plug 74 to be easily dislodged from the outflow end portion 68. For example, in some embodiments, the plug 74 can comprise an axial thickness that is less than a width 79 of the wall 62 of the shunt 60. Further, in some embodiments, the plug 74 can comprise an axial thickness that is about equal to the width 79 of the wall 62 of the shunt 60. Thus, in some embodiments, the thickness of the plug 74 can be from about 30 μm to about 80 from about 40 μm to about 50 or about 45 μm.

Furthermore, the width 79 of the wall can be as much as two, three, or four times as great as the width 78 of the plug 74. Accordingly, in some embodiments, the thickness of the plug 74 can be from about 7 μm to about 40 from about 10 μm to about 25 or about 15 μm.

However, in some embodiments, the width 78 of the plug 74 can be greater than the width 79 of the wall 62. For example, the width 78 of the plug 74 can be as much as two, three, or four times as great as the width 79 of the wall 62. Moreover, relative to an overall length of the shunt itself, the width 78 of the plug 74 can be between about 0.1% to about 40%, between about 30% to about 40%, between about 20% to about 30%, between about 15% to about 20%, between about 10% to about 15%, between about 5% to about 10%, between about 3% to about 5%, between about 2% to about 3%, between about 1% to about 2%, between about 0.5% to about 1%, between about 0.1% to about 0.5%, between about 0.2% to about 0.5%, or between about 0.3% to about 0.4% of the overall length of the shunt. Accordingly, in some embodiments, the plug 74 can have a width 78 of from about 8 μm to about 3200 μm, from about 16 μm to about 2400 μm, from about 24 μm to about 1600 μm, from about 32 μm to about 1200 μm, from about 40 μm to about 800 μm, from about 80 μm to about 400 μm, or from about 160 μm to about 240 μm.

As illustrated in FIG. 4, in some embodiments, the plug 74 can extend across the outflow end portion 68. The plug 74 can be positioned entirely within the lumen 64. However, the plug 74 can also cover a portion of the end surfaces of the outflow end portion 68.

In some embodiments, in order to form the shunt 60, the shunt 60 can be dipped into a solution to permit capillary action or wicking forces to draw the solution into the lumen 64 to form a plug therewithin. Alternatively, the solution can be injected or pulled into the lumen 64. However, the plug 74 can also be inserted into the lumen 64 as a solid material that is held in place by a friction fit or adhesion.

As illustrated further below and FIGS. 10A-10D, which illustrate an embodiment similar to that shown in FIGS. 3 and 4, the plug 74 can be dislodged and displaced from within the lumen 64 in order to permit flow through the lumen 64. Accordingly, in some embodiments, the outflow end portion 68 of the shunt 60 can be flexible and deformable in response to a compressive load. The compressive load applied to the outflow end portion 68 can shift or move the wall 62 of the shunt 60, thereby dislodging the plug 74 by overcoming the frictional or adhesive engagement between an outer surface 76 of the plug 74 and an inner surface of the lumen 64. As the outer surface 76 of the plug 74 slips relative to the inner surface of the lumen 64, the plug 74 can be ejected from the lumen 64, thereby clearing the obstruction created by the plug 74.

As noted above, in some embodiments, the inner diameter of the shunt 60 can remain the same, increase, or decrease when hydrated. Further, in some embodiments, the inner diameter of the shunt 60 can increase while a removable portion or plug 74 (providing the flow restriction at the outflow end portion or restrictive section 70) coupled to or residing within the restrictive section 70 of the lumen 64 expands at a lower rate or to a lesser degree than the inner diameter of the shunt 60. Thus, after implantation and hydration of the shunt 60, and after a desired period of time has passed (which can be configured based on the formulation of the shunt and the removable portion), the plug 74 may be in a "burstable" state. In addition, or alternatively, the shunt 60 and/or the plug 74 can degrade at differing rates to permit the plug 74 to be in the burstable state. In the burstable state, the plug 74 may have a reduced engagement with the outflow end portion 68, thus permitting the plug 74 to be more easily dislodged or ruptured upon application of an external force, such as a compressive force.

Similarly, FIG. 5 illustrates an intraocular shunt 80 that comprises an elongate body having a wall 82 that defines a shunt lumen 84 extending therethrough. The shunt 80 can comprise opposing end portions (e.g., an inlet end portion 86 and an outflow end portion 88). The inlet end portion 86 can be clear and permit flow thereinto, and the outflow end portion 88 can comprise one or more restrictions. The shunt 80 can comprise an obstructive or flow-limiting restrictive section 90 and an unobstructive or unrestrictive main section 92. The shunt lumen 84 can extend through the main section 92. In the illustrated embodiment, flow through the restrictive section 90 is occluded or blocked.

The restrictive section 90 can comprise a flow restrictor or cap 94 that is positioned around the outflow end portion 88 (and may extend at least partially within the lumen 84) of the shunt 80. The cap 94 can comprise a mass of material that is coated onto and dried around the outflow end portion 88. For example, in some embodiments, the shunt 80 can be dipped into a solution that coats the outflow end portion 88 to form a cap or stopper on the outflow end portion 88 of the shunt 80. However, the cap 94 can also be coupled to the outflow end portion 88 as a solid material or layer that is held in place by a friction fit or adhesion.

As noted above with respect to FIGS. 3, 4, and FIGS. 10A-10D, the cap 94 can be dislodged and displaced from outflow end portion 88 of the shunt 80 in order to permit flow through the lumen 84. Thus, in some embodiments, the outflow end portion 88 of the shunt 80 can be flexible and deformable in response to a compressive load. The compressive load applied to the outflow end portion 88 can shift or move the wall 82 of the shunt 80, thereby dislodging the cap 94 by overcoming the frictional or adhesive engagement between the cap 94 and an outer surface of the shunt 80. As the cap 94 slips relative to the outer surface of the shunt 80, the cap 94 can be separated from the outflow end portion 88 of the shunt 80, thereby clearing the obstruction created by the cap 94.

In some embodiments, the cap 94 can comprise an outer cross-sectional profile that is greater than an outer diameter of the shunt 80. The cap 94 can comprise one or more proximal protruding surfaces 96 that extend outwardly from an outer surface 98 of the shunt 80. The protruding surfaces 96 can allow a force (e.g., a compressive force) applied by a clinician to more easily cause axial displacement of the cap 94 relative to the shunt 80 when the clinician is dislodging the cap 94.

Moreover, in some embodiments, the cap 94 can advantageously comprise an axial thickness (measured along the longitudinal axis) that tends to ensure that the cap 94 has a greater compressive strength or resistance to compression than the shunt 80. Accordingly, as a compressive force is applied against the shunt 80 and the cap 94, the shunt 80 will tend to radially deform or compress to a greater degree than the cap 94. Such action can thus tend to cause disengagement between the outflow end portion 88 of the shunt 80 and the cap 94.

Further, in some embodiments, the outer diameter of the shunt 80 can remain the same, increase, or decrease when hydrated. In some embodiments, the outer diameter of the shunt 80 can remain the same or increase while a removable portion or cap 94 (providing the flow restriction at the outflow end portion or restrictive section 90) coupled to or covering the restrictive section 90 of the lumen 84 expands at a higher rate or to a greater degree than the outer diameter of the shunt 80. Thus, after implantation and hydration of the shunt 80, and after a desired period of time has passed (which can be configured based on the formulation of the shunt and the removable portion), the cap 94 may be in a "burstable" state. In addition, or alternatively, the shunt 80 and/or the cap 94 can degrade at differing rates to permit the cap 94 to be in the burstable state. In the burstable state, the cap 94 may have a reduced engagement with the outflow end portion 88, thus permitting the cap 94 to be more easily dislodged or ruptured upon application of an external force, such as a compressive force.

Figure 6:
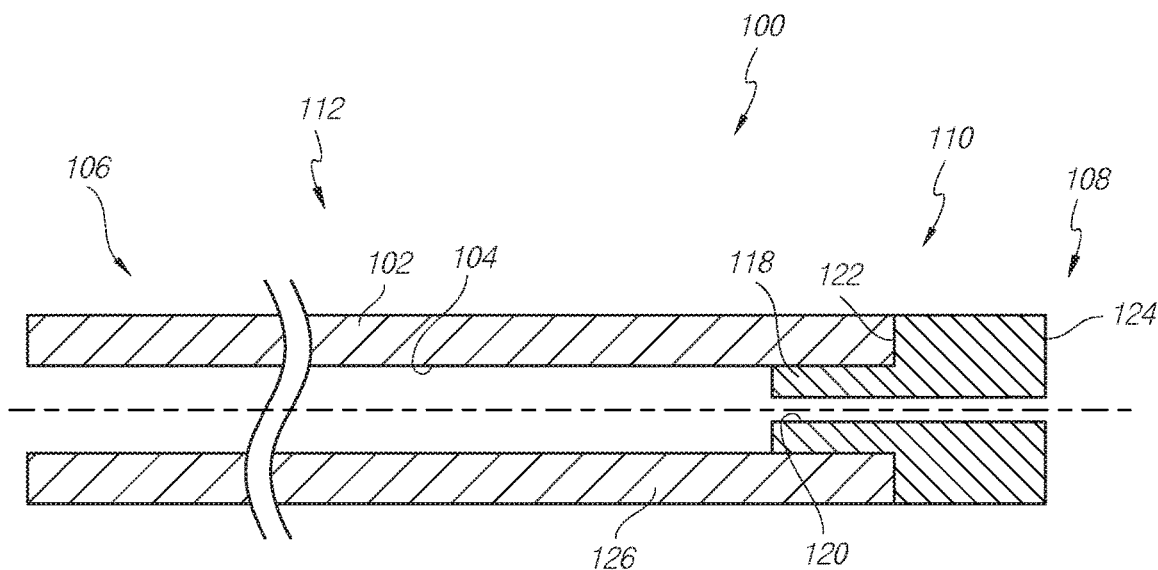

FIG. 6 illustrates a shunt 100 having an elongate body having a wall 102 that defines a shunt lumen 104 extending therethrough. The shunt 100 can comprise opposing end portions (e.g., an inlet end portion 106 and an outflow end portion 108). The inlet end portion 106 can be clear and permit flow thereinto, and the outflow end portion 108 can comprise one or more restrictions. The shunt 100 can comprise an obstructive or flow-limiting restrictive section 110 and an unobstructive or unrestrictive main section 112. Flow can be provided through the restrictive section 110, but with greater resistance than through the main section 112. The shunt lumen 104 can extend through the main section 112. The restrictive section 110 can comprise a gelatin tube. The gelatin tube can be inserted into the shunt lumen 104.

FIG. 6 illustrates the restrictive section 110 of the shunt 100 in greater detail. The restrictive section 110 or gelatin tube can comprise a wall 118 that defines a secondary lumen 120. The wall 118 can define a different inner dimension than the wall 102. For example, the wall 118 can define a cross-section or profile that is smaller than the cross-section or profile of the wall 102, thus rendering the lumen 104 larger than the lumen 120. In some embodiments, the secondary lumen 120 can extend generally coaxially with the shunt lumen 104; however, the secondary lumen 120 can be configured to be spaced apart from a central axis of the shunt lumen 104.

For example, the secondary lumen 120 can also extend longitudinally along the restrictive section 110 while traversing and/or being spaced apart from the central axis of the restrictive section 110. The wall 118 can define a constant or variable thickness. Further, the secondary lumen 120 can be at least partially encircled by the wall 118 forming the restrictive section 110. However, the wall 118 can be discontinuous, and the secondary lumen 120 can be bounded intermediate the wall 118 of the restrictive section 110 and the wall 102. Thus, the lumen 104 and the lumen 120 can have a boundary surface in common, in some embodiments.

In some embodiments, as shown in FIG. 6, the restrictive section 110 can be shaped as a plug that is configured such that the wall 110 defines an outer diameter that is about equal to the inner diameter of the shunt lumen 104. As such, the plug can be inserted into the lumen 104 to couple the plug to the main section 112.

Further, the restrictive section 110 can be removably coupled to the main section 112, such as to permit the clinician to manually dislodge, separate, or remove the restrictive section 110 from the outflow end portion 108 of the shunt 100. For example, the restrictive section 110 can be removably coupled to the main section 112, thereby allowing the restrictive section 110 to be completely or at least partially removed from the main section 112. For example, the restrictive section 110 can comprise a metal stylus or structure that is inserted into the shunt lumen 104, which can later be removed.

Additionally, the restrictive section 110 can comprise a gelatin material that is the same or different from the main section 112. For example, the restrictive section 110 can comprise a material that has a different degradation rate than that of the main section 112, which can be accomplished by having more or less cross-linking, additional materials, or other structures that facilitate removal or degradation of the restrictive section 110 from the main section 112.

Furthermore, in some embodiments, the restrictive section can be formed using a material or component that is formed separately from the restrictive end portion and later joined or coupled thereto. For example, the restrictive section can be adhered, chemically joined, or mechanically coupled, such as by a friction or interference fit, or by mating engagement between complementary structures, such as protrusions and detents.

To facilitate dislodgement, the restrictive section 110 can include an enlarged portion 124 with a restrictive end portion 122 that abuts against the inlet end portion 106. The enlarged portion 124 can remain at least partially outside of the lumen 104 to allow dislocation, separation, or removal of the restriction section 110, as described herein. As shown in FIG. 6, the secondary lumen 120 of the restrictive section 110 continues through the enlarged portion 124. In some embodiments, the enlarged portion 124 can have a cross-section or outer profile that is similar to that of the wall 102. Further, in some embodiments, the restrictive section 110 can be a solid plug devoid of or without a lumen extending therethrough.

The shunt 100 can be configured such that two or more sections thereof comprise different flow restrictions or flow values. Thus, in some instances, a clinician can manually manipulate or adjust the overall flow restriction or flow value of the shunt 100 by manipulating one or more sections of the shunt 100. In some embodiments, this manipulation can be performed without surgery. Further, in some embodiments, a clinician can utilize a shunt or shunt system that self-adjusts or passively adjusts to change the overall flow restriction or flow value of the shunt over time.

The flow resistance or flow value of a given section of the shunt can relate to the geometric constraints or properties of the given section. The geometric constraints or properties can be one or more of the diameter or radius, the length of the given section, a cross-sectional area of the flow passage, surface roughness, or other such geometrics characteristics. In some embodiments, for purposes of this disclosure, the flow resistance or flow value can be a numeric representation, coefficient, or formula upon which the mathematical calculation for a fluid flow rate through the given section for a given fluid is predicated. For example, the flow value can represent a ratio of an inner diameter or radius and an axial length of the given section. A higher flow value could result in a higher flow rate. Further, in some embodiments, the flow resistance can be the inverse of the flow value, e.g., a ratio of an axial length and an inner diameter or radius of the given section. Generally, a higher flow resistance would result in a lower flow rate. Further, the flow resistance can depend mainly on the shunt length, inner diameter and viscosity of the liquid (aqueous humor).

The flow through the shunt, and thus the pressure exerted by the fluid on the shunt, is calculated by the Hagen-Poiseuille equation:

$$\Phi = \frac{dV}{dt} = v\pi R^2 = \frac{\pi R^4}{8\eta}\left(\frac{-\Delta P}{\Delta x}\right) = \frac{\pi R^4}{8\eta}\frac{|\Delta P|}{L}$$

where $\Phi$ is the volumetric flow rate; V is a volume of the liquid poured (cubic meters); t is the time (seconds); v is mean fluid velocity along the length of the tube (meters/second); $\Delta x$ is a distance in direction of flow (meters); R is the internal radius of the tube (meters); $\Delta P$ is the pressure difference between the two ends (pascals); $\eta$ is the dynamic fluid viscosity (pascalsecond (Pa·s)); and L is the total length of the tube in the x direction (meters).

For example, the shunt 100 can be configured such that the flow through the restrictive section 110 defines a flow resistance or flow value. The main section 112 can define a first flow cross-sectional area, and the restrictive section 110 can define a second flow cross-sectional area that is less than the first flow cross-sectional area. The first flow resistance or flow value can be determined by geometric constraints or properties of the restrictive section 110. Such constraints can include the length of the restrictive section 110, the inner diameter or radius of the wall 118, and other features, such as an inner surface roughness of the wall 118.

Further, the second flow cross-sectional area or profile of the restrictive section 110 can be any of a variety of geometric profiles. For example, the second flow cross-sectional area or profile can be circular, rectangular, square, polygonal, or otherwise shaped. The second flow cross-sectional area or profile can be configured to provide less cross-sectional area than the main section 112. The second flow cross-sectional area or profile can be constant or variable along the longitudinal extent of the restrictive section 110.

Similarly, the main section 112 can define a flow resistance or flow value that is different than the first flow resistance or flow value of the restrictive section 110. As with the flow resistance or flow value of the restrictive section 110, the flow resistance or flow value of the main section 112 can be determined by geometric constraints or properties of the main section 112, as discussed above. Accordingly, the geometric constraints of the main section 112 can differ from the geometric constraints of the restrictive section 110, resulting in different flow resistances or flow values.

The total pressure drop across the shunt $\Delta P_{total}$ consisting of a main section and a partially constrained section can be calculated for each section separately as $\Delta P_{main}$ and $\Delta P_{partially\ constrained}$, according to the formula above:

$$\Delta P = \frac{8\Phi\eta L}{\pi R^4}$$

and then by adding the two numbers together: $\Delta P_{total} = \Delta P_{main} + \Delta P_{partially\ constrained}$. If there are more than 2 sections, then they are added together accordingly.

$\Delta P_{total}$ for any given shunt represents the minimum IOP in the eye for any given flow rate $\Phi$. The flow rate $\Phi$ through the shunt is depending on the shunt location and amount of surrounding tissue resistance normally from about 10% to about 90% of the amount of aqueous production in the eye which is typically from about 1 to about 3 µl/min.

As illustrated in FIG. 6, the shunt 100 can comprise a single restrictive section 110 and a single main section 112. However, the shunt 100 can comprise multiple restrictive sections and/or multiple main sections (see e.g., FIGS. 7-9).

A given restrictive section can also define a plurality of cross-sectional flow areas or inner diameters. For example, as illustrated in FIG. 7, the restrictive section can have distinct steps or subsections that have distinct cross-sectional flow areas or inner diameters.

Figure 7:
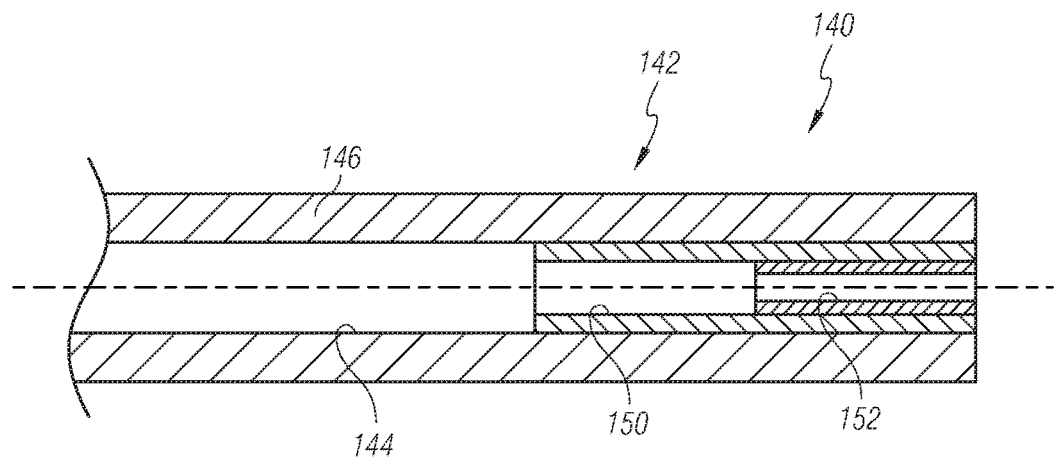

FIG. 7 illustrates an embodiment of a shunt 140 in which an obstructive or flow-limiting restrictive section 142 comprises first and second occluding components 150, 152. The first occluding component 150 and the second occluding component 152 can be inserted into a lumen 144, formed by a shunt wall 146 of the shunt 140. The first and second occluding component 150, 152 can also be pre-assembled prior to insertion into the shunt lumen 144. The first and second occluding components 150, 152 can define different inner cross-sectional dimensions (e.g., diameters) that provide distinct flow resistances or flow values. Accordingly, in some embodiments, a clinician can manually dislodge, separate, or remove more than one restrictive section in order to adjust the flow resistance or flow value of the shunt, thus enabling the clinician to achieve two or more different flow resistances or flow values through the shunt. For example, an initial manual manipulation, such as that discussed below with regard to FIGS. 10A-10D, can be applied to dislodge, separate, or remove the second occluding component 152 from the first occluding component 150, thus leaving only the first occluding component 150 coupled to the shunt 140. Thereafter, the clinician can optionally dislodge, separate, or remove the first occluding component 150 from the shunt 140 by further application of manual manipulation.

For example, similar to the embodiment illustrated in FIG. 7, the restrictive section can be formed using a tube configured to fit within the shunt lumen. Further, the restrictive section can be formed using a component, coating, or other material that is layered along the inner surface of the shunt wall. The component, coating, or other material can extend at least partially about the circumference of the inner surface of the shunt wall. In some embodiments, the component, coating, or other material can extend fully about the circumference, and in some embodiments, the component, coating, or other material can extend longitudinally along the inner surface of the shunt wall. In any configuration, the overall cross-sectional flow area of the restrictive section can be less than the overall cross-sectional flow area of the main section.

In some embodiments, a restrictive section can be formed by varying a dimension of the shunt along that restrictive section. Further, the restrictive section can be demarcated from the main section at a joint by perforations, a thin shunt wall, or other such structures to permit preferential degradation or breakage at the joint. Thus, the restrictive section can be formed integrally or of a single, continuous piece of material with the main section of the shunt.

Figure 8:
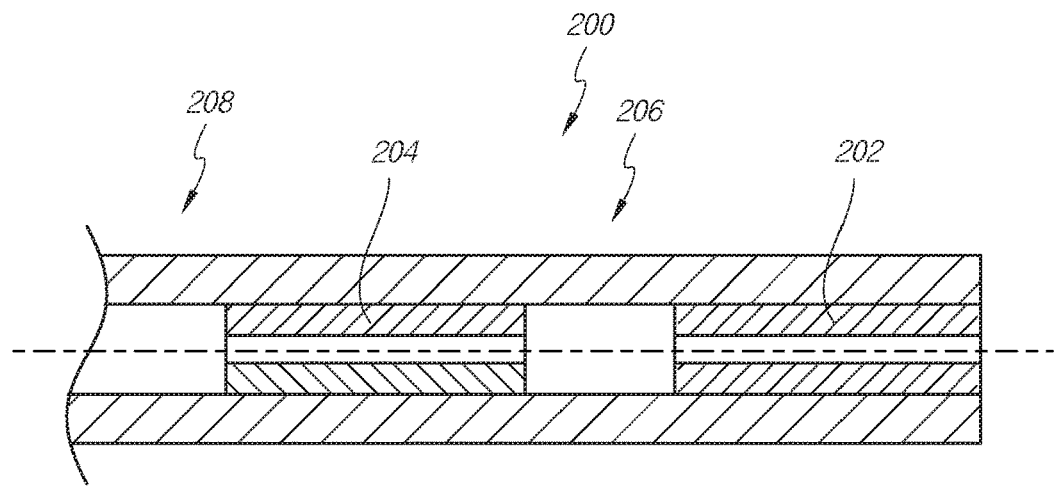

FIG. 8 illustrates yet another embodiment of a shunt 200 having a plurality of obstructive or flow-limiting restrictive sections 202, 204 and a plurality of main sections 206, 208. The restrictive sections 202, 204 can comprise identical or different flow resistances or flow values. As illustrated, the restrictive section 202 can define a slightly longer axial length than the restrictive section 204. Accordingly, the flow resistance for the restrictive section 202 can be greater than the flow resistance for the restrictive section 204. In some embodiments, the inner diameter or radius of the restrictive sections 202, 204 can also vary. Further, the main section 206 can be disposed between the restrictive sections 202, 204.

As noted above with respect to the embodiment shown in FIG. 7, the restrictive sections 202, 204 can be manually manipulated by a clinician to separate one or both of the restrictive sections 202, 204 from the shunt 200. Accordingly, a nonsurgical intervention can be performed to adjust the flow value of the shunt 200, similar to that discussed below with respect to FIGS. 10A-10D.

As with any of the geometric parameters of embodiments taught or disclosed herein, other features and aspects of the shunt 200 can be very, such as the distance between the obstructive or flow-limiting restrictive sections 202, 204, in order to achieve a desired overall flow resistance or flow value for the shunt.

Figure 9:
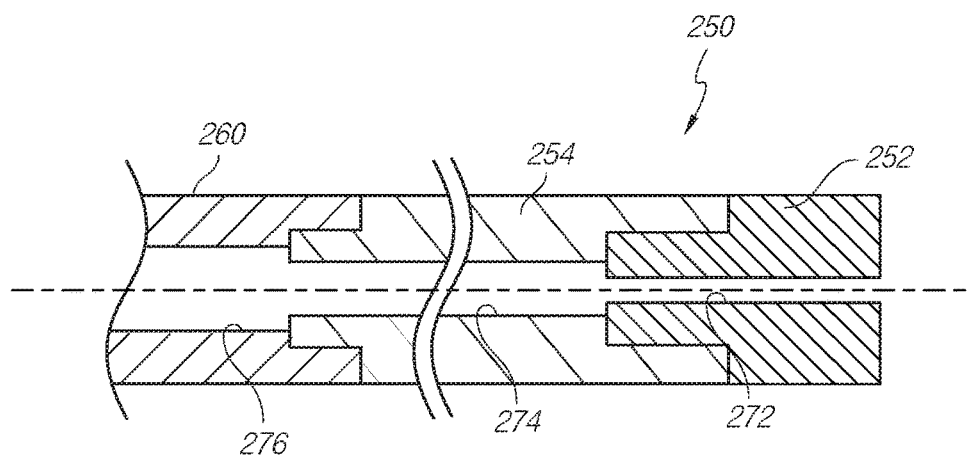

Additionally, FIG. 9 illustrates an embodiment similar to FIG. 6, discussed above. In FIG. 9, a shunt 250 is illustrated that comprises first and second restrictive sections 252, 254 that can be removably coupled to each other and to a main section 260 of the shunt 250. FIG. 9 illustrates that the first and second restrictive sections 252, 254 comprise different internal diameters, 272, 274, which can also be different from the internal diameter 276 of the main section 260. However, the first and second restrictive sections 252, 254 and the main section 260 can have the same or different internal diameters as each other.

As noted above with regard to the embodiments shown in FIGS. 3-8, a clinician can manually manipulate the shunt 250 in order to dislodge, separate, or remove one or both of the restrictive sections 252, 254 from the main body 260 of the shunt 250.

In any of the embodiments disclosed herein, a clinician can be enabled to perform a single or multiple incremental manual, nonsurgical interventions that can change the flow resistance of the shunt. Other configurations or combinations of the shunts illustrated in FIGS. 3-9 can be performed and are contemplated as part of the present disclosure.

Using a flow-tunable shunt disclosed or taught herein, a clinician can perform a manual, nonsurgical intervention in order to modify the flow resistance or flow value of one or more portions of the shunt to adjust the overall flow resistance or flow value of the shunt. This allows the clinician to ensure that the shunt maintains an optimal overall flow resistance in response to any increase in biological outflow resistance. Thus, during postoperative visits, the clinician can monitor any changes in the tissue surrounding the shunt or the drainage channels, measure and track the intraocular pressure, and when necessary, adjust or modify the flow resistance or flow value in order to maintain an optimal intraocular pressure.

As noted above, after a shunt is placed in the eye has healed, the surrounding tissue can create biological outflow resistance, such as fibrosis, which can limit or reduce the flow through the shunt. The tissue reaction that changes the overall outflow resistance of the shunt typically stabilizes after about 1-10 weeks after the surgery.

A clinician can conduct a post-operative checkup to modify the shunt in a subsequent procedure after a threshold period of time has passed. This period of time can be from about eight weeks to about three months. Often, ten weeks can be a sufficient amount of time in order to achieve stabilization and healing. If appropriate, the modification of the shunt can be performed as a matter of course.

As part of the post-operative checkup, the clinician can verify whether the intraocular pressure is at a desired level. Generally, normal intraocular pressure is from about 10 mmHg and about 20 mmHg. Should the intraocular pressure be at an undesirable level (e.g., greater than 20 mmHg), the clinician can modify the shunt accordingly.

The clinician can modify the shunt to reduce the flow resistance or flow value of the shunt. For example, the clinician can remove a portion from the shunt, and in some cases, remove a portion thereof from the eye. The dislocation, separation, or removal of a portion of the shunt can decrease the flow resistance of the shunt and thereby permit increased flow through the shunt, relieving and reducing the intraocular pressure.

Accordingly, in some embodiments, methods and devices are provided by which a shunt can provide: (1) substantial initial outflow resistance in order to avoid early low post-op intraocular pressures and hypotony, and (2) the ability to subsequent reduce outflow resistance to compensate for a rising biological outflow resistance (e.g., fibrosis of the targeted space).

In order to change the flow resistance or flow value of the shunt, some embodiments of the shunt can be configured such that the clinician can manually manipulate the shunt, through a nonsurgical intervention, in order to remove one or more aspects, sections, or all of the obstructive or flow-limiting restrictive section(s) of the shunt. In some instances, the clinician can dislodge, separate, or remove a restrictive portion of the shunt and thereby open up the flow for an optimal long-term intraocular pressure performance.

In some methods, the shunt can be positioned such that a restrictive end portion is disposed in the anterior chamber of the eye. Further, in some methods, the shunt can be positioned such that a restrictive end portion is disposed in the targeted space or a location of lower pressure. Furthermore, in some embodiments, the shunt can be configured and positioned such that one or more obstructive or flow-limiting restrictive sections or end portions are situated in the anterior chamber and the targeted space.

In accordance with some embodiments, the shunt can be positioned such that the restrictive end portion thereof is positioned in the targeted space or location of lower pressure, such as in the subconjunctival space of the eye. For example, FIGS. 10A-10D illustrate a shunt 380 that is implanted into an eye 302. The shunt 380 can comprise an inflow end portion 386 and an outflow end portion 384. The inflow end portion 386 can be positioned in the anterior chamber 310 of the eye 302. Further, the outflow end portion 384 can be placed in the subconjunctival space 320 of the eye 302. Thus, the shunt 380 can be operative to provide pressure relief of the fluid in the anterior chamber 310 to a location of lower pressure, such as the subconjunctival space 320 of the eye 302. As noted above, while an obstructive or flow-limiting restrictive section 382 disposed in the outflow end portion 384 can tend to ensure that the condition of low intraocular pressure is avoided, such as hypotony, over time, certain biological outflow restrictions can be formed, which can reduce the overall outflow or flow rate of the shunt 380. The restrictive section 382 can be coupled to the shunt 380, such as by being at least partially disposed within a lumen 383 of the shunt 380. The embodiment of the shunt 380 shown in FIGS. 10A-10D is similar to that illustrated above and FIG. 6. As discussed further below, FIGS. 10A-10D illustrate the steps by which a clinician can manually manipulate the restrictive section 382 within the shunt 380 to adjust the flow resistance or flow value of the shunt 380 without surgical intervention.

Figure 10A:
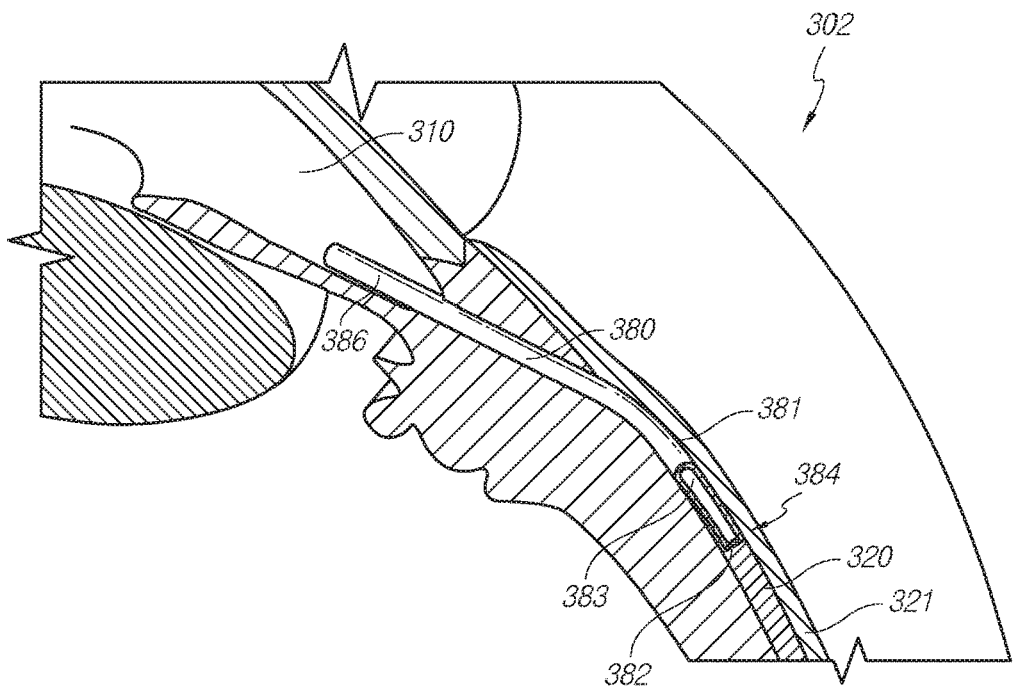
FIGS. 10A-10D illustrate the dislodging of a portion of a removable portion of a shunt, according to some embodiments.

FIGS. 10A-10D illustrate different aspects of embodiments in which the shunt 380 can be mechanically modified. FIG. 10A illustrates the shunt 380 in an initial position or configuration whereat the flow resistance through the shunt is at a maximum. After a clinician determines that a reduction in flow resistance is warranted, the physician can then ascertain the position of the shunt 380 relative to the structures of the eye 302 and prepare to manipulate or modify the configuration of the shunt 380.

Figure 10B:
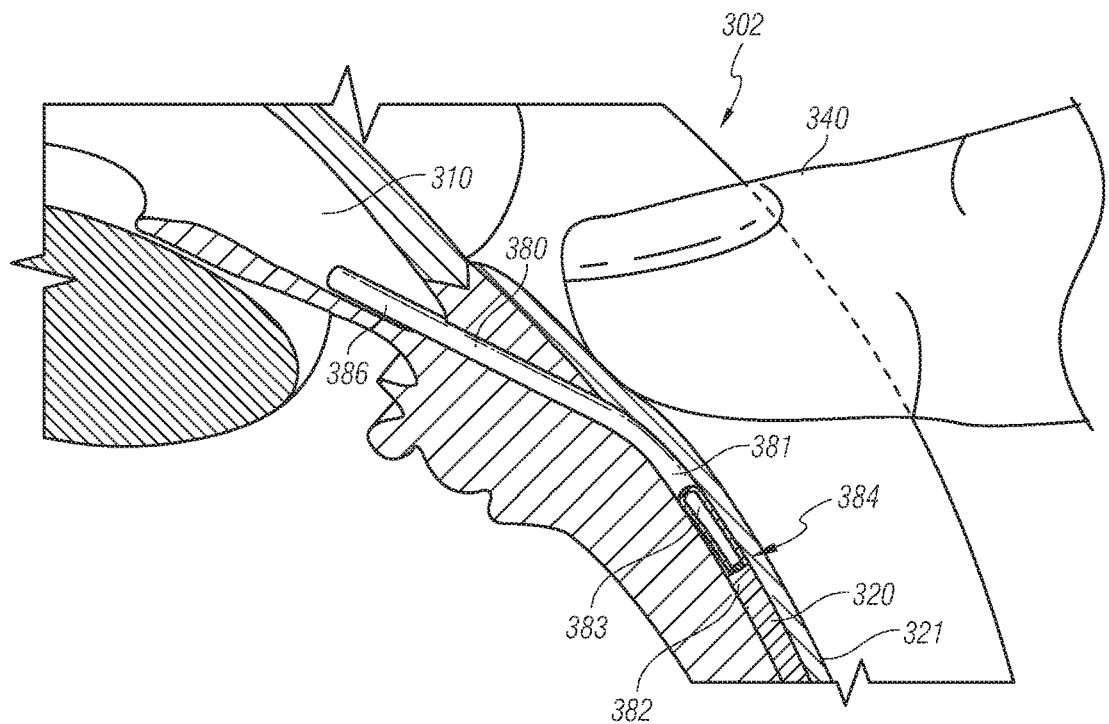
Figure 10C:
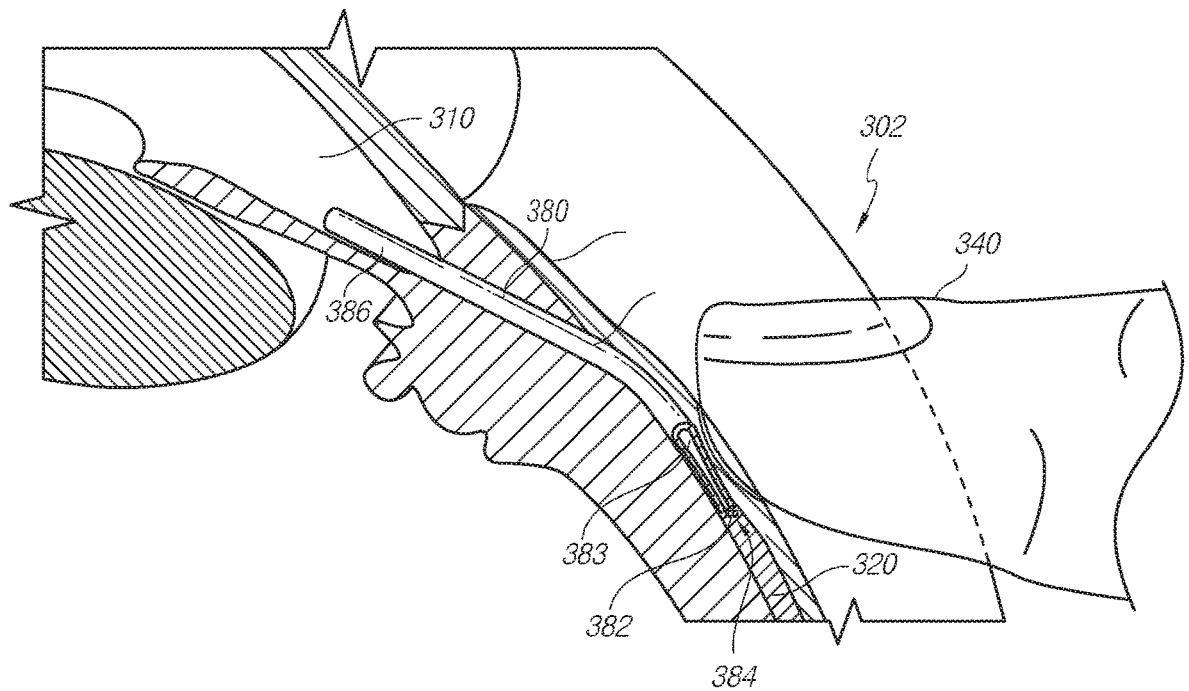

For example, FIGS. 10B and 10C illustrate the stroke of a clinician's finger in performing a nonsurgical method for mechanically modifying the shunt 380 in order to adjust the flow resistance or flow value of the shunt 380. As illustrated, the restrictive portion 382 can be removed from the outflow end portion 384 the shunt 380 by pressing against the conjunctiva 321, applying a pressure against the eye, and moving the finger and a posterior direction along the conjunctiva 321 above the shunt 380.

As discussed above, in some embodiments, the restrictive section 382 can comprise a fluid restriction that can be removed the lumen 383 of the shunt 380. Further, the restrictive section 382 can be removably attached to the inside of the lumen 383 of the shunt 380. In some embodiments, the restrictive section 382 can comprise a plug, a reduced cross section portion, or any other suitable occlusion. The restrictive section 382 can be fully disposed within the shunt 380, or at least partially externally disposed around the shunt 380. The restrictive section 382 can be removed from the shunt 380 by overcoming the adhesive or the frictional retention of the restrictive section 382 within the shunt 380.

In accordance with some embodiments, the restrictive section 382 can be removed from within the shunt 380 by applying a force to the exterior surface 381 of the shunt 380 by deforming the shunt 380.

In some embodiments, the shunt 380 is formed from a material that is flexible and/or otherwise compressible. For example, pressure or force can be applied to the exterior surface 381 of the shunt 380 to compress, flex, or otherwise deform the shunt 380. In some embodiments, as the force is applied to the exterior surface 381 of the shunt 380, the interior cross section of the shunt 380 can be reduced from an initial cross section to a compressed or reduced cross section.

In some embodiments, the restrictive section 382 disposed within the shunt 380 may not compress as much as the shunt 380 when external force is applied to the exterior surface 381 of the shunt 380. For example, the restrictive section 382 can comprise a structural strength different from that of the shunt 380, such as a thicker wall, different material, or other such structural variant. Therefore, as the shunt 380 is deformed, the restrictive section 382 can be urged away from the area with the reduced cross section to an area with a greater cross section or out of the shunt 380. In some embodiments, the restrictive section 382 can be slid through the shunt 380 by applying a force anterior to the restrictive section 382 and directed in a posterior direction to reduce the cross section anterior to the restrictive section 382 and squeeze or urge the restrictive section 382 out of the shunt lumen 383 or otherwise apart from the shunt 380.

In some embodiments, external force can be applied directly to the exterior surface 381 of the shunt 380 to deform the shunt 380. In some embodiments, an external force can be applied to tissues of the eye 302, which can compress or otherwise transmit the force to the external surface 381 of the shunt 380, as shown in FIG. 10C. In the depicted example, the shunt 380 is located in the subconjunctival area 320. Therefore, force can be applied to the conjunctiva 321 to compress the conjunctiva 321 and transmit a force to the exterior surface 381 of the shunt 380.

Figure 10D:
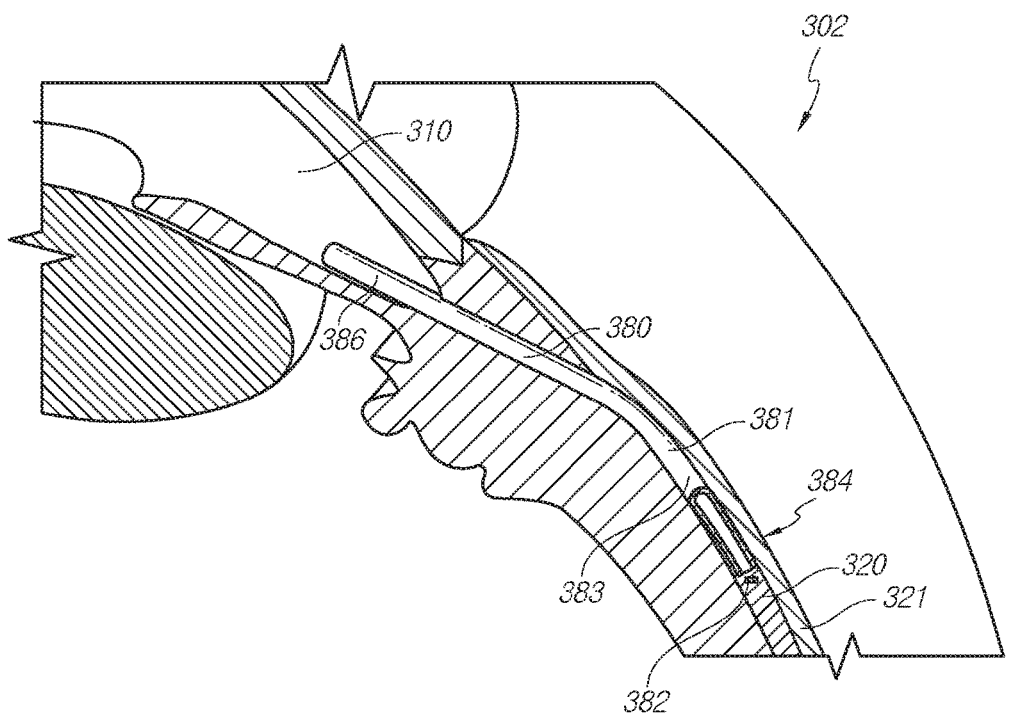

As shown in FIGS. 10B and 10C, in the depicted example, a clinician can apply force to the eye 302 with a finger 340 to massage the eye tissue, such as the conjunctiva 321, to compress the shunt 380. This compression of the shunt 380 can force the restrictive section 382 out of the restrictive end portion 384 to be spaced apart from the shunt 380 in the subconjunctival space 320, as illustrated in FIG. 10D.

As shown in FIG. 10C, in some embodiments, as the restrictive section 382 is urged out of the shunt 380, the restrictive section 382 can be urged out the outflow end portion 384. In some embodiments, after the restrictive section 382 is urged out of the shunt 380, the restrictive section 382 can be spaced apart from the outflow end portion 384 such that a small space is present between the restrictive section 382 and the outflow end portion 384, as shown in FIG. 10D. In this manner, outflow through the outflow end portion 384 can generally remain clear. In some embodiments, the restrictive section 382 can be removed from the eye or left in place to act as a spacer that will tend to prevent blockage and preserve outflow through the outflow end portion 384. This can be particularly true for a restrictive section 382 material that remains very quiet in the eye, such as a gelatin material. In some embodiments, the restrictive portion 382 can be spaced apart from the outflow end portion 384 by from about 0.2 mm to about 2 mm. Further, the restrictive portion 382 can be spaced apart from the outflow end portion 384 by from about 0.5 mm to about 1 mm.

In some embodiments, after the restrictive portion 382 is spaced apart from the outflow end portion 384, the restrictive portion 382 can be extracted from the eye 302.

Figure 11:
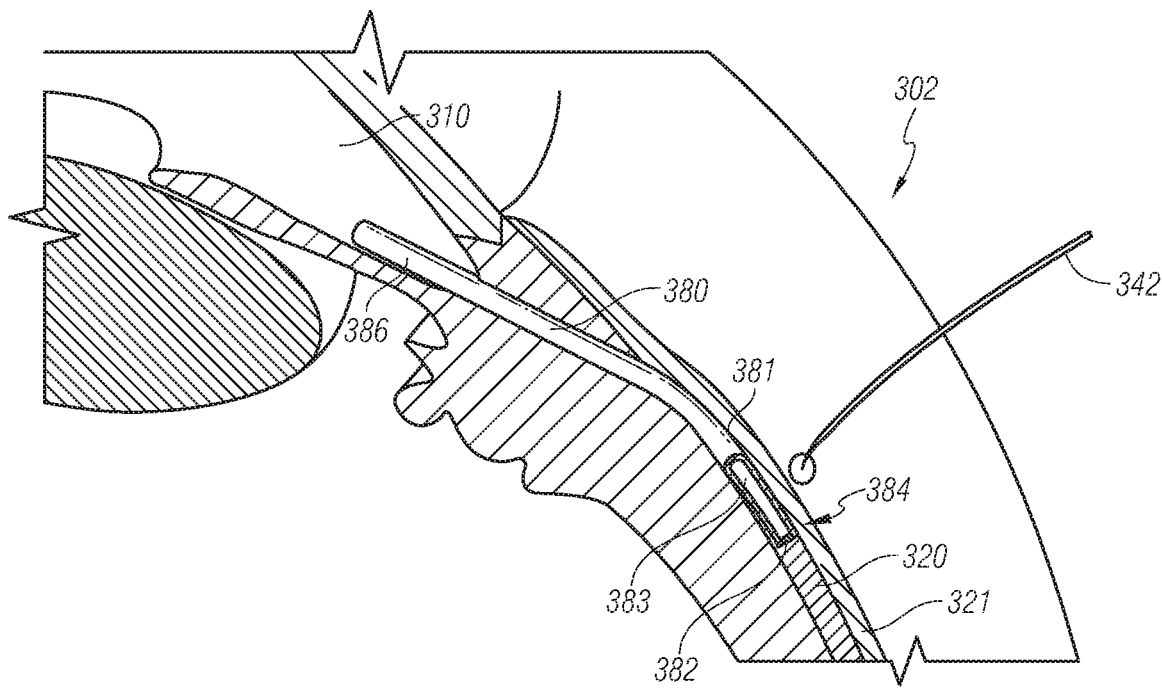
FIG. 11 illustrates the dislodging of a portion of the removable portion of a shunt, using a tool, according to some embodiments.

Referring to FIG. 11, in the depicted example, instead of a finger, a roller tool 342 can be used to apply force or massage the eye 302. In some embodiments, by utilizing a roller tool 342, a force can be applied to the eye 302 while minimizing shear force imparted to the eye 302. The roller tool 342 can be any suitable tool suitable for use on an eye 302.

Figure 12:
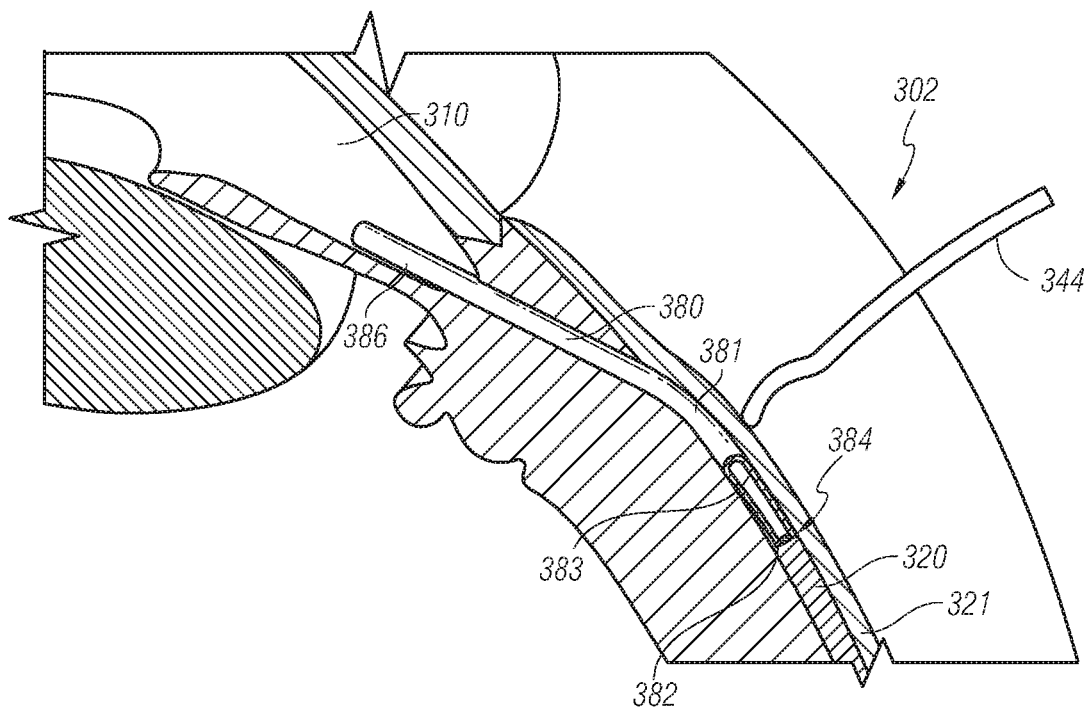
FIG. 12 illustrates the dislodging of a portion of the removable portion of a shunt, using another tool, according to some embodiments.

Referring to FIG. 12, a wedge tool 344 can be used to apply a force or massage the eye 302. In some embodiments, by utilizing the wedge tool 344, pressure or force can be applied to the eye 302 while providing some shear force to urge the restrictive section 382 out of the shunt 380. In some embodiments, the wedge tool 344 can also be in the form of a flat paddle (not shown) that can be used to apply a wide area of force against the eye 302.

In some embodiments, the restrictive section 382 can be removed by applying force directly to the restrictive section 382. In some embodiments, the restrictive section 382 can be pulled or otherwise urged out of the lumen 383.

Figure 13:
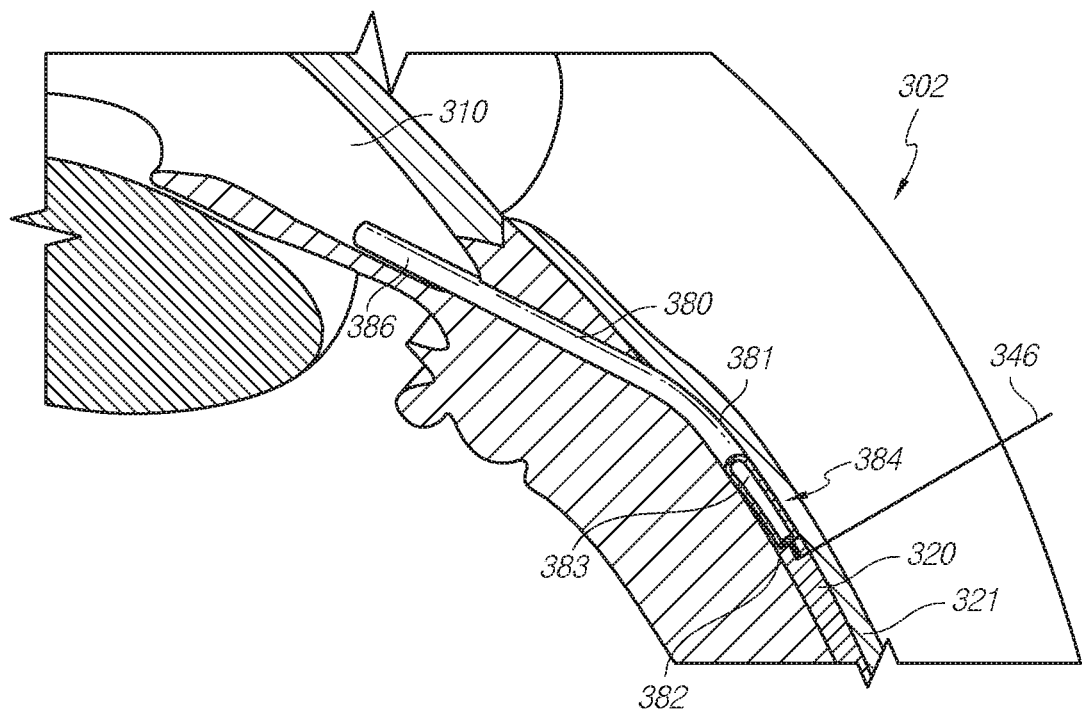
FIG. 13 illustrates the removal of a portion of the removable portion of a shunt, using yet another tool, according to some embodiments.

Some embodiments can also provide a method or device that uses a minimally invasive surgical procedure to dislodge and/or remove a restrictive section of the shunt. For example, referring to FIG. 13, in the depicted example, the restrictive section 382 can be dislodged, separated, or removed from the shunt 380 without any manipulation of the exterior surface 381 of shunt 380.

In some embodiments, a retrieval tool 346 can be used to pierce the conjunctiva and engage the restrictive section 382. The tool 346 can then slide the restrictive section 382 out of the shunt 380. The retrieval tool 346 can grab or otherwise engage the restrictive section 382 and allow a clinician to pull out the restrictive section 382 after overcoming a frictional and/or adhesion force within the lumen 383.

In some embodiments, the retrieval tool 346 can comprise a scalpel, hypodermic needle, or other surgical tool.

Additional methods and devices can also be provided in which a flow-tunable shunt provides early hypotony protection and a later, gradual lessening of the flow restriction without any post-op surgical intervention (such as those discussed herein). In some embodiments, whether used independently of or in conjunction with other aspects of embodiments disclosed herein, the shunt can also comprise an unobstructive or unrestrictive main section and an obstructive, restrictive, or flow-limiting dissolvable plug or section. The main section and/or the restrictive section can also be detachable or separable from the shunt, as discussed in embodiments above. Such dissolvable plugs are sections can be incorporated into and used in addition to any of the plugs, caps, or other removable portions of the embodiments discussed above.

The shunt can be configured such that flow can move more easily through the main section than through the restricted section. The main section can comprise a wall that defines a first flow cross-sectional area. The restrictive dissolvable section can comprise a wall that defines an aperture, lumen, or channel through which fluid can pass, but with greater resistance than through the main section. Thus, in some embodiments, the presence of a dissolvable section can slow, but not entirely restrict flow through the shunt. Instead, a dissolvable section can be located so as to restrict flow at early stages after the surgical procedure, but to dissolve over time, thereby increasing flow through the dissolvable section and hence, through the shunt.

In some embodiments, the shunt can comprise one or more restrictive dissolvable sections. For example, the shunt can comprise a restrictive dissolvable section at a single end portion thereof. The shunt can comprise two or more restrictive dissolvable sections, spaced close together or spaced apart from each other at opposing end portions of the shunt. In some methods, a restrictive dissolvable section can be placed either in the anterior chamber or in an area of lower pressure, such as the subconjunctival space. An aspect of some embodiments is the realization that there may be an advantage to placing a dissolvable section in the anterior chamber (compared with having the dissolvable section only in the subconjunctival space) due to the possibility that particulate or debris could float into the shunt lumen and block flow through a dissolvable section in the subconjunctival space.

Further, the restrictive section(s) can comprise a wall that defines an aperture, lumen, or channel. As noted similarly with regard to other embodiments above, the wall of the restrictive section(s) can define a second flow cross-sectional area. The second flow cross-sectional area can be less than the first flow cross-sectional area of the main section. In some embodiments, the wall(s) can define aperture(s), lumen(s), or channel(s) that are generally tubular. Further, the aperture(s), lumen(s), or channel(s) can be square, polygonal, triangular, or other varieties of random shapes. The wall(s) can be configured such that the aperture(s), lumen(s), or channel(s) can extend along a central axis of the restrictive section(s). However, the aperture(s), lumen(s), or channel(s) can also extend longitudinally along the restrictive section while traversing and/or spaced apart from the central axis of the restrictive section. Further, the aperture(s), lumen(s), or channel(s) can be encircled by the material forming the restrictive section. However, the aperture(s), lumen(s), or channel(s) can also be formed intermediate the wall of the restrictive section and the wall of the main section.

Additionally, the material forming the restrictive dissolvable section(s) of the shunt can be configured to dissolve according to a desired dissolution rate, dissolution order, and/or dissolution pattern. A restrictive dissolvable section can comprise more than one type of material. The material(s) can be layered axially, circumferentially offset, or otherwise positioned to provide a differential or staged dissolution order or pattern. The material(s) can have variable or different dissolution rates.

All or only a portion of a shunt may be dissolvable. For example, the dissolvable section can comprise a dissolvable biocompatible material. The material can be configured to dissolve over a set or desired period of time, from days to months, based on how long hypotony protection is desired.

In some embodiments, the material selected for the shunt or the restrictive section can comprise a gelatin or other similar material. In some embodiments, the gelatin used for making the shunt can comprise a gelatin Type B from bovine skin. A preferred gelatin is PB Leiner gelatin from bovine skin, Type B, 225 Bloom, USP. Another material that may be used in the making of the shunts is a gelatin Type A from porcine skin, also available from Sigma Chemical. Such gelatin is available is available from Sigma Chemical Company of St. Louis, Mo. under Code G-9382. Still other suitable gelatins include bovine bone gelatin, porcine bone gelatin and human-derived gelatins. In addition to gelatins, microfistula shunt may be made of hydroxypropyl methylcellulose (HPMC), collagen, polylactic acid, polylglycolic acid, hyaluronic acid and glycosaminoglycans.

The shunt material can be cross-linked. For example, when a gelatin is used, cross-linking can increase the inter- and intramolecular binding of the gelatin substrate. Any means for cross-linking the gelatin may be used. In some embodiments, the formed gelatin shunts can be treated with a solution of a cross-linking agent such as, but not limited to, glutaraldehyde. Other suitable compounds for cross-linking include 1-ethyl-3-[3-(dimethyamino)propyl]carbodiimide (EDC). Cross-linking by radiation, such as gamma or electron beam (e-beam) may be alternatively employed.

The dissolvable section can comprise a material that is identical, similar, or different from the material of the shunt.

In some embodiments, the dissolvable section material can be made out of a gelatin, which can be similar to a gelatin used to make the shunt, with the gelatins differing in the amount of crosslinking each has undergone.

In some embodiments, the shunt can be cross-linked by contacting the shunt with a solution of about 25% glutaraldehyde for a selected period of time. One suitable form of glutaraldehyde is a grade 1G5882 glutaraldehyde available from Sigma Aldridge Company of Germany, although other glutaraldehyde solutions may also be used. The pH of the glutaraldehyde solution should preferably be in the range of 7 to 7.8 and, more preferably, 7.35-7.44 and typically about 7.4.+−.0.01. If necessary, the pH may be adjusted by adding a suitable amount of a base such as sodium hydroxide as needed.

For example, a "permanent" implant can be crosslinked by keeping it in a 25% Gluderaldehyde solution for 16 hours. This saturates the crosslinking and results in a permanent implant that does not dissolve over any meaningful time frame (e.g., 10 years). However, in such embodiments, a gelatin that has undergone much less crosslinking (using a lower crosslinking time and/or a lower Gluderaldehyde concentration) can be used for the dissolvable section. By lowering the crosslinking time and/or the amount of Gluderaldehyde concentration, less than complete crosslinking can be achieved, which results in a dissolving material over an adjustable time frame. Other dissolvable materials and other crosslinking techniques can be used to provide the dissolvable section.

According to some methods, by adjusting the Gluderaldehyde concentration, crosslinking time, crosslinking temperature and/or the geometry of the dissolvable section, the dissolving time can be from at least about 15 minutes to several years. The dissolving time can also be from at least about 1 hour to several months. For example, a completely non-crosslinked gelatin dissolvable section can dissolve in about 20 minutes. Therefore, the Gluderaldehyde concentration, crosslinking time, and/or the geometry (longitudinal length, aperture or channel size, etc.) of the dissolvable section can be modified accordingly to adjust the dissolution rate of the dissolvable section.

Regarding the design considerations for shunt inner dimension or diameter and length and dissolvable section length and channel dimensions, longer "pipes" have higher fluid resistance and fluid resistance decreases as "pipe" radius and cross-sectional area increase. Specifically, flow and resulting pressure values can be determined using formulas known in the art. The flow rate for flow through a tube having different interior cross sections can be calculated using such formulas. Calculating laminar flow through a tube can be performed using the Hagen-Poiseuille equation discussed above. Assuming that the flow restriction of a large lumen shunt is insignificant, the pressure difference ΔP between the shunt entrance and exit is given by the length L and the inner diameter (radius R) of the plugged/constricted part of the shunt only.

Additionally, in accordance with some methods, the shunt may be made by dipping a core or substrate such as a wire of a suitable diameter in a solution of material, such as gelatin. In some methods, in order to form shunts having one or more restrictive sections (e.g., dissolvable portions), a core or substrate can be configured to include one or more peaks, valleys, protrusions, and/or indentations corresponding to the desired inner profile of the shunt. The core or substrate can be coated or dipped multiple times in order to become coated with a desired number of layers or materials. For example, a core or substrate can have a first section having a small outer diameter and a second section having a large outer diameter. The section having a smaller outer diameter can be coated or dipped in a solution such that the outer diameter along the first section is generally equal to the large outer diameter of the second section. Thereafter, the first and second sections of the core or substrate can be immersed in a solution and dried. When removed, the shunt can therefore have an inner diameter that narrows in a restricted section thereof, which corresponds to the first section of the core or substrate. Other details and features of methods of preparing and fabricating a shunt are disclosed in U.S. Application Publication Nos. 2012/0197175, filed on Dec. 8, 2011, and 2013/0150770, filed on Dec. 8, 2011, the entireties of each of which are incorporated herein by reference.

In the case of a gelatin implant, the solution can be prepared by dissolving a gelatin powder in de-ionized water or sterile water for injection and placing the dissolved gelatin in a water bath at a temperature of about 55° C. with thorough mixing to ensure complete dissolution of the gelatin. In one embodiment, the ratio of solid gelatin to water is about 10% to 50% gelatin by weight to 50% to 90% by weight of water. In some embodiments, the gelatin solution includes about 40% by weight, gelatin dissolved in water. The resulting gelatin solution preferably is devoid of any air bubbles and has a viscosity that is from about 200 cp (centipoise) to about 500 cp. The solution can also have a viscosity from about 260 to about 410 cp.

As discussed further herein, the gelatin solution may include biologics, pharmaceuticals, drugs, and/or other chemicals selected to regulate the body's response to the implantation of the shunt and the subsequent healing process. Examples of suitable agents include anti-mitolic pharmaceuticals such as Mitomycin-C or 5-Fluorouracil, anti-VEGF (such as Lucintes, Macugen, Avastin, VEGF or steroids), anti-coagulants, anti-metabolites, angiogenesis inhibitors, or steroids. By including the biologics, pharmaceuticals, drugs, or other chemicals in the liquid gelatin, the formed shunt will be impregnated with the biologics, pharmaceuticals, drugs, or other chemicals.

In accordance with some embodiments, the shunt can comprise a drug or drug-eluting portion for drug delivery to one or more target locations within the eye. A drug-eluting portion can be provided in combination with any of the embodiments disclosed or taught herein. For example, the shunt can comprise a drug-eluting portion. Thus, some embodiments provide a shunt that also operates as a drug delivery device inside the eye.

One or more drugs can be carried by the shunt for delivery to the target location(s). The shunt itself can carry a drug and can be partially or completely dissolvable. For example, one or more drugs can be carried in one or more dissolvable coating(s) along a surface of the shunt. The drug-eluting dissolvable coating(s) can extend along the entire length or only a portion of the length of the shunt. The drug(s) can also be carried as a component of a dissolvable section, according to some embodiments. In some embodiments, a time controlled drug release can be achieved by configuring the dissolvable coating or portion to provide a desired dissolution rate. Such drug-eluting portion(s) of the shunt can therefore provide a drug delivery, even without aqueous flow.

Aspects related to embodiments of drug delivery shunts are discussed in co-pending U.S. Publication No. 2012/0197175, filed on Dec. 8, 2008, the entirety of which is incorporated herein by reference.

Various types of drugs can be used, including, glaucoma drugs, steroids, other anti-inflammatory, antibiotics, dry eye, allergy, conjunctivitis, etc.

At least a section of the shunt can comprise one or more drugs to provide a drug-eluting portion. In some embodiments, one or more drugs can be provided along the entire length of the shunt. However, in some embodiments, one or more drugs can be provided along less than the entire shunt or along only a portion of the shunt. For example, a drug can be integrated into only one of the ends of the shunt to provide a single drug-eluting end which can be placed into the anterior chamber or location of lower pressure. Further, other than being formed along an end portion of the shunt, the drug-eluting portion can also be formed along an intermediate portion of the shunt. Accordingly, some embodiments can provide a targeted drug release inside the anterior chamber, inside the sclera, and/or in the subconjuctival space, depending on the location and configuration of the drug-eluting portion(s).

In some embodiments, the shunt can comprise multiple drug-eluting portions, which can each be formed to provide different dissolving times and/or have different drugs embedded therein. Accordingly, in some embodiments, two or more drugs can be delivered simultaneously on independent release timings.

For example, the shunt can comprise multiple dissolvable sections, which can each be formed to provide different dissolving times and/or have different drugs embedded therein.

The shunt can also be implanted into the suprachoroidal space (which one end portion in the anterior chamber and the other end portion in the suprachoroidal space or with the entire shunt being completely suprachoroidal) with the ability to deliver drugs at either or both end portions or along an intermediate portion thereof. Some methods can be implemented such that multiple shunts (with the same or different drugs and with the same or different release timings) can be implanted in different places (e.g., the subconjunctival space, the suprachoroidal space, the anterior chamber, etc.).

Tissue Compatible Shunts

In some embodiments, the shunt can comprise a material that has an elasticity modulus that is compatible with an elasticity modulus of tissue surrounding the shunt. For example, the intraocular shunt can be flexible, and have an elasticity modulus that is substantially identical to the elasticity modulus of the surrounding tissue in the implant site. As such, some embodiments of the intraocular shunt can be easily bendable, may not erode or cause a tissue reaction, and may not migrate once implanted.

Accordingly, when implanted in the eye using an ab interno procedure, such as some methods described herein, some embodiments of the intraocular shunt may not induce substantial ocular inflammation such as subconjunctival blebbing or endophthalmitis. Additional exemplary features of embodiments of the intraocular shunt are discussed in further detail below. In this manner, some embodiments of the shunt can be configured to have a flexibility compatible with the surrounding tissue, allowing the shunt to remain in place after implantation without the need for any type of anchor that interacts with the surrounding tissue. Consequently, some embodiments of the shunt can thereby maintain fluid flow away from an anterior chamber of the eye after implantation without causing irritation or inflammation to the tissue surrounding the eye.

As discussed in applicant's co-pending application, U.S. Publication No. 2013/0150770, filed on Dec. 8, 2011, the entirety of which is incorporated herein by reference, elastic modulus or the modulus of elasticity, is a mathematical description of an object or substance's tendency to be deformed elastically when a force is applied to it. See also Gere (Mechanics of Materials, 6th Edition, 2004, Thomson) (the content of which is incorporated by reference herein in its entirety). The elasticity modulus of a body tissue can be determined by one of skill in the art. See, e.g., Samani et al. (Phys. Med. Biol. 48:2183, 2003); Erkamp et al. (Measuring The Elastic Modulus Of Small Tissue Samples, Biomedical Engineering Department and Electrical Engineering and Computer Science Department University of Michigan Ann Arbor, Mich. 48109-2125; and Institute of Mathematical Problems in Biology Russian Academy of Sciences, Pushchino, Moscow Region 142292 Russia); Chen et al. (IEEE Trans. Ultrason. Ferroelec. Freq. Control 43:191-194, 1996); Hall, (In 1996 Ultrasonics Symposium Proc., pp. 1193-1196, IEEE Cat. No. 96CH35993, IEEE, New York, 1996); and Parker (Ultrasound Med. Biol. 16:241-246, 1990), the contents of each of which are incorporated by reference herein in its entirety.

The elasticity modulus of tissues of different organs is known in the art. For example, Pierscionek et al. (Br J Ophthalmol, 91:801-803, 2007) and Friberg (Experimental Eye Research, 473:429-436, 1988), both incorporated by reference herein in their entirety, show the elasticity modulus of the cornea and the sclera of the eye. Chen, Hall, and Parker show the elasticity modulus of different muscles and the liver. Erkamp shows the elasticity modulus of the kidney.

In some embodiments, the shunt can comprise a material that has an elasticity modulus that is compatible with the elasticity modulus of tissue in the eye, particularly scleral tissue. In some embodiments, compatible materials are those materials that are softer than scleral tissue or marginally harder than scleral tissue, yet soft enough to prohibit shunt migration. The elasticity modulus for anterior scleral tissue is about $2.9 \pm 1.4 \times 106$ N/m2, and $1.8 \pm 1.1 \times 106$ N/m2 for posterior scleral tissue. In some embodiments, the material can comprise a gelatin. In some embodiments, the gelatin can comprise a cross-linked gelatin derived from Bovine or Porcine Collagen. Further, the shunt can comprise one or more biocompatible polymers, such as polycarbonate, polyethylene, polyethylene terephthalate, polyimide, polystyrene, polypropylene, poly(styrene-b-isobutylene-b-styrene), or silicone rubber.

As discussed in Applicant's co-pending application, U.S. Publication No. 2013/0150770, filed on Dec. 8, 2011, and in U.S. Publication No. 2012/0197175, filed Dec. 8, 2011, the entireties of each of which is incorporated herein by reference, some embodiments of the shunt can comprise optional features. For example, some embodiments can comprise a flexible material that is reactive to pressure, i.e., the dimension or diameter of the flexible portion of the shunt fluctuates depending upon the pressures exerted on that portion of the shunt. Further, the shunt can comprise one or more side ports. Additionally, some embodiments of the shunt can also comprise overflow ports. Some embodiments of the shunt can also comprise one or more prongs at an end thereof in order to facilitate conduction of fluid flow away from an organ. In accordance with some embodiments, the shunt can also be configured such that an end of the shunt includes a longitudinal slit. Other variations and features of the shunt can be incorporated into embodiments disclosed herein.

In addition to providing a safe and efficient way to relieve intraocular pressure in the eye, it has been observed that implanted shunts disclosed herein can also contribute to regulating the flow rate (due to resistance of the lymphatic outflow tract) and stimulate growth of functional drainage structures between the eye and the lymphatic and/or venous systems. These drainage structures evacuate fluid from the subconjunctiva which also result in a low diffuse bleb, a small bleb reservoir or no bleb whatsoever.

The formation of drainage pathways formed by and to the lymphatic system and/or veins may have applications beyond the treatment of glaucoma. Thus, the methods of shunt implantation may be useful in the treatment of other tissues and organs where drainage may be desired or required.

In addition, it has been observed that as a fully dissolvable shunt absorbs, a "natural" microfistula shunt or pathway lined with cells is formed. This "natural" shunt is stable. The implanted shunt stays in place (thereby keeping the opposing sides of the formed shunt separated) long enough to allow for a confluent covering of cells to form. Once these cells form, they are stable, thus eliminating the need for a foreign body to be placed in the formed space.

Deployment into the eye of an intraocular shunt according to this disclosure can be achieved using a hollow shaft configured to hold the shunt, as described herein. The hollow shaft can be coupled to a deployment device or part of the deployment device itself. Deployment devices that are suitable for deploying shunts according to the invention include, but are not limited to the deployment devices described in U.S. Pat. Nos. 6,007,511, 6,544,249, and U.S. Publication No. 2008/0108933, the contents of each of which are incorporated herein by reference in their entireties. In other embodiments, the deployment devices can include devices such as those as described in co-pending and co-owned U.S. Publication No. 2012/0123434, filed on Nov. 15, 2010, U.S. Publication No. 2012/0123439, filed on Nov. 15, 2010, and co-pending U.S. Publication No. 2013/0150770, filed on Dec. 8, 2011, the contents of each of which are incorporated by reference herein in their entireties.

Although the detailed description contains many specifics, these should not be construed as limiting the scope of the subject technology but merely as illustrating different examples and aspects of the subject technology. It should be appreciated that the scope of the subject technology includes other embodiments not discussed in detail above. Various other modifications, changes and variations may be made in the arrangement, operation and details of the method and apparatus of the subject technology disclosed herein without departing from the scope of the present disclosure. Unless otherwise expressed, reference to an element in the singular is not intended to mean "one and only one" unless explicitly stated, but rather is meant to mean "one or more." In addition, it is not necessary for a device or method to address every problem that is solvable by different embodiments of the disclosure in order to be encompassed within the scope of the disclosure.

Illustration of Subject Technology as Clauses

Various examples of aspects of the disclosure are described below as clauses for convenience. These are provided as examples, and do not limit the subject technology.

Clause 1. A method of adjusting a flow rate of an intraocular shunt implanted in an eye, the method comprising: determining a position of the intraocular shunt in the eye extending between an anterior chamber of the eye and a location of lower pressure of the eye; and applying a force to an outer surface of the eye to separate or displace a removable portion relative to an outflow portion of the intraocular shunt, thereby permitting an increased flow rate through the intraocular shunt.

Clause 2. The method of claim 1, wherein the removable portion comprises a first inner cross-sectional dimension and the intraocular shunt comprises a second inner cross-sectional dimension greater than the first inner cross-sectional dimension, and wherein the applying a force comprises compressing the second inner cross-sectional dimension to be smaller than the first inner cross-sectional dimension.

Clause 3. The method of any preceding clause, wherein the applying a force comprises increasing a permitted flow rate from about zero to a nonzero flow rate.

Clause 4. The method of any preceding clause, wherein the applying a force comprises increasing a permitted flow rate from a nonzero flow rate.

Clause 5. The method of any preceding clause, wherein the applying a force comprises positioning the removable portion in a location spaced apart from an exit of the outflow portion after separating the removable portion from the intraocular shunt.

Clause 6. The method of Clause 5, further comprising extracting the removable portion from the eye after separating the removable portion from the outflow portion.

Clause 7. The method of any preceding clause, wherein the outflow portion is located in a subconjunctival space of the eye.

Clause 8. The method of Clause 7, wherein the applying a force comprises applying a force to a conjunctiva of the eye to apply a force to the outer surface of the eye.

Clause 9. The method of any preceding clause, wherein at least a portion of the removable portion is disposed internally within the intraocular shunt.

Clause 10. The method of any preceding clause, wherein before the applying a force, the removable portion is disposed at least partially external to the shunt.

Clause 11. The method of any preceding clause, further comprising permitting the removable portion to degrade in the location of lower pressure after applying a force to the outer surface of the eye.

Clause 12. The method of any preceding clause, wherein the removable portion comprises a degradable material, a viscoelastic material, or any combination thereof.

Clause 13. The method of any preceding clause, wherein the removable portion comprises a plurality of removable portions.

Clause 14. The method of any preceding clause, wherein the removable portion comprises a drug.

Clause 15. The method of any preceding clause, wherein the applying a force to the outer surface of the eye comprises applying a force via a finger.

Clause 16. The method of any preceding clause, wherein the applying a force to the outer surface of the eye comprises applying a force via a tool.

Clause 17. The method of Clause 16, wherein the tool comprises a roller tool.

Clause 18. The method of Clause 16, wherein the tool comprises a wedge tool.

Clause 19. A method of adjusting a flow rate of an intraocular shunt, the method comprising: inserting the intraocular shunt into an eye, such that an inflow portion of the intraocular shunt is located in an anterior chamber of the eye and an outflow portion of the intraocular shunt is located in a location of lower pressure of the eye, the outflow portion of the intraocular shunt being restricted with a removable portion when inserted into the location of lower pressure; and after the inserting, applying a force to the location of lower pressure to dislodge the removable portion from the outflow portion of the intraocular shunt to change a flow rate through the intraocular shunt.

Clause 20. The method of Clause 19, wherein the removable portion comprises a first inner cross-sectional dimension and the intraocular shunt comprises a second inner cross-sectional dimension greater than the first inner cross-sectional dimension, and wherein the applying a force comprises compressing the second inner cross-sectional dimension to be smaller than the first inner cross-sectional dimension.

Clause 21. The method of any one of Clauses 19-20, wherein the applying a force comprises increasing a permitted flow rate from about zero to a nonzero flow rate.

Clause 22. The method of any one of Clauses 19-21, wherein the applying a force comprises increasing a permitted flow rate from a nonzero flow rate.

Clause 23. The method of any one of Clauses 19-22, wherein the applying a force comprises positioning the removable portion in a location spaced apart from an exit of the outflow portion after dislodging the removable portion from the intraocular shunt.

Clause 24. The method of Clause 23, further comprising extracting the removable portion from the eye after dislodging the removable portion from the outflow portion.

Clause 25. The method of any one of Clauses 19-24, wherein the outflow portion is located in a subconjunctival space of the eye.

Clause 26. The method of Clause 25, wherein the applying a force comprises applying a force to a conjunctiva of the eye to apply a force to the location of lower pressure.

Clause 27. The method of any one of Clauses 19-26, wherein at least a portion of the removable portion is disposed internally within the intraocular shunt.

Clause 28. The method of any one of Clauses 19-27, wherein before applying a force, the removable portion is disposed at least partially external to the shunt.

Clause 29. The method of any one of Clauses 19-28, further comprising permitting the removable portion to degrade in the location of lower pressure after applying a force to the location of lower pressure.

Clause 30. The method of any one of Clauses 19-29, wherein the removable portion comprises a degradable material, a viscoelastic material, or any combination thereof.

Clause 31. The method of any one of Clauses 19-30, wherein the removable portion comprises a plurality of removable portions.

Clause 32. The method of any one of Clauses 19-31, wherein the removable portion comprises a drug.

Clause 33. The method of any one of Clauses 19-32, wherein the inserting the intraocular shunt into the eye comprises inserting the intraocular shunt via an ab externo approach.

Clause 34. The method of any one of Clauses 19-33, wherein the inserting the intraocular shunt into the eye comprises inserting the intraocular shunt via an ab interno approach.

Clause 35. The method of any one of Clauses 19-34, wherein the applying a force to the location of lower pressure comprises applying a force via a finger.

Clause 36. The method of any one of Clauses 19-35, wherein the applying a force to the location of lower pressure comprises applying a force via a tool.

Clause 37. The method of Clause 36, wherein the tool comprises a roller tool.

Clause 38. The method of Clause 36, wherein the tool comprises a wedge tool.

Clause 39. A method of adjusting a flow rate of an intraocular shunt implanted in an eye, the method comprising: determining a position of an outflow end of the intraocular shunt underlying a conjunctiva of the eye, the shunt being operative to permit flow of aqueous humor from an anterior chamber of the eye; and massaging the outflow end of the shunt to dislodge a plug from a lumen of the shunt thereby modifying a flow rate through the shunt.

Clause 40. The method of Clause 39, wherein the plug comprises a first inner cross-sectional dimension and the intraocular shunt comprises a second inner cross-sectional dimension greater than the first inner cross-sectional dimension, and wherein the massaging the outflow end comprises compressing the second inner cross-sectional dimension to be smaller than the first inner cross-sectional dimension.

Clause 41. The method of any one of Clauses 39-40, wherein the massaging the outflow end comprises increasing a permitted flow rate from about zero to a nonzero flow rate.

Clause 42. The method of any one of Clauses 39-41, wherein the massaging the outflow end comprises increasing a permitted flow rate from a nonzero flow rate.

Clause 43. The method of any one of Clauses 39-42, wherein the massaging the outflow end comprises positioning the plug in a location spaced apart from an exit of the outflow end after dislodging the plug from the lumen.

Clause 44. The method of Clause 43, further comprising extracting the plug from the eye after dislodging the plug from the outflow end.

Clause 45. The method of any one of Clauses 39-44, wherein the outflow end is located in a subconjunctival space of the eye.

Clause 46. The method of any one of Clauses 39-45, wherein the massaging the outflow end comprises massaging the conjunctiva of the eye to massage the outflow end of the intraocular shunt.

Clause 47. The method of any one of Clauses 39-46, wherein at least a portion of the plug is disposed internally within the intraocular shunt.

Clause 48. The method of any one of Clauses 39-47, wherein before the massaging the outflow end, the plug is disposed at least partially external to the shunt.

Clause 49. The method of any one of Clauses 39-48, further comprising permitting the plug to degrade after massaging the outflow end.

Clause 50. The method of any one of Clauses 39-49, wherein the plug comprises a degradable material, a viscoelastic material, or any combination thereof.

Clause 51. The method of any one of Clauses 39-50, wherein the plug comprises a plurality of plugs.

Clause 52. The method of any one of Clauses 39-51, wherein the plug comprises a drug.

Clause 53. The method of any one of Clauses 39-52, further comprising inserting the intraocular shunt into the eye, such that an inflow portion of the intraocular shunt is located in the anterior chamber of the eye.

Clause 54. The method of Clause 53, wherein inserting the intraocular shunt into the eye comprises inserting the intraocular shunt via an ab externo approach.

Clause 55. The method of Clause 53, wherein inserting the intraocular shunt into the eye comprises inserting the intraocular shunt via an ab interno approach.

Clause 56. The method of any one of Clauses 39-55, wherein massaging the outflow end comprises applying a mechanical force to the plug.

Clause 57. The method of Clause 56, wherein massaging the outflow end of the shunt comprises applying a force to the conjunctiva of the eye to dislodge the plug from the lumen.

Clause 58. The method of Clause 57, wherein the applying a force to the conjunctiva comprises applying a force via a finger.

Clause 59. The method of Clause 57, wherein the applying a force to the conjunctiva comprises applying a force via a tool.

Clause 60. The method of Clause 59, wherein the tool comprises a roller tool.

Clause 61. The method of Clause 59, wherein the tool comprises a wedge tool.

Clause 62. The method of Clause 56, wherein the applying the mechanical force to the plug comprises applying the mechanical force via a tool.

Clause 63. The method of Clause 62, wherein the tool is a retrieval tool.

Clause 64. A shunt for draining fluid from an anterior chamber of an eye, the shunt comprising: a main section having an inflow end portion, an outflow end portion, and wall defining a lumen, a removable portion coupled to the outflow end portion to block flow through the lumen when present, the removable portion providing a burstable seal across the outflow end portion and being configured to rupture upon application of compressive force against the shunt, wherein rupture of the removable portion permits fluid to flow through the lumen from the anterior chamber into the inflow end portion toward the outflow end portion such that, when positioned in the eye, fluid is released through the outflow end portion at a location having lower pressure than the anterior chamber.

Clause 65. The shunt of Clause 64, wherein the removable portion comprises a disk-shaped membrane coupled to the outflow end portion.

Clause 66. The shunt of Clause 65, wherein the wall of the main section comprises a first thickness and the membrane comprises a second thickness, the first thickness being greater than the second thickness.

Clause 67. The shunt of Clause 65, wherein the wall of the main section comprises a first thickness and the membrane comprises a second thickness, the first thickness being equal to the second thickness.

Clause 68. The shunt of Clause 65, wherein the wall of the main section comprises a first thickness and the membrane comprises a second thickness, the first thickness being less than three times the second thickness.

Clause 69. The shunt of any one of Clauses 65-68, wherein the membrane is positioned within the lumen.

Clause 70. The shunt of any one of Clauses 65-68, wherein the membrane comprises a plug.

Clause 71. The shunt of Clause 64, wherein the removable portion has a bulbous shape and overlaps an outer surface of the shunt adjacent to the outflow end portion.

Clause 72. The shunt of Clause 71, wherein the removable portion comprises an outer cross-sectional profile greater than an outer diameter of the shunt.

Clause 73. The shunt of any one of Clauses 64-72, wherein the removable portion comprises a first material and the main section comprises a second material different from the first material.

Clause 74. The shunt of any one of Clauses 64-73, wherein the removable portion is dissolvable.

Clause 75. The shunt of any one of Clauses 64-74, wherein the shunt comprises a cross-linked gelatin.

Clause 76. The shunt of any one of Clauses 64-75, wherein the removable portion comprises an axial thickness of about 0.1% to about 40% of an overall length of the shunt.

Clause 77. The shunt of any one of Clauses 64-76, wherein the removable portion comprises an axial thickness of about 30% to about 40% of an overall length of the shunt.

Clause 78. The shunt of any one of Clauses 64-77, wherein the removable portion comprises an axial thickness of about 20% to about 30% of an overall length of the shunt.

Clause 79. The shunt of any one of Clauses 64-78, wherein the removable portion comprises an axial thickness of about 15% to about 20% of an overall length of the shunt.

Clause 80. The shunt of any one of Clauses 64-79, wherein the removable portion comprises an axial thickness of about 10% to about 15% of an overall length of the shunt.

Clause 81. The shunt of any one of Clauses 64-80, wherein the removable portion comprises an axial thickness of about 5% to about 10% of an overall length of the shunt.

Clause 82. The shunt of any one of Clauses 64-81, wherein the removable portion comprises an axial thickness of about 3% to about 5% of an overall length of the shunt.

Clause 83. The shunt of any one of Clauses 64-82, wherein the removable portion comprises an axial thickness of 2% to about 3% of an overall length of the shunt.

Clause 84. The shunt of any one of Clauses 64-83, wherein the removable portion comprises an axial thickness of 1% to about 2% of an overall length of the shunt.

Clause 85. The shunt of any one of Clauses 64-75, wherein the removable portion comprises an axial thickness of about 8 μm to about 3200 μm.

Clause 86. The shunt of any one of Clauses 64-75 or 85, wherein the removable portion comprises an axial thickness of about 16 μm to about 2400 μm.

Clause 87. The shunt of any one of Clauses 64-75 or 85-86, wherein the removable portion comprises an axial thickness of about 24 μm to about 1600 μm.

Clause 88. The shunt of any one of Clauses 64-75 or 85-87, wherein the removable portion comprises an axial thickness of between about 30 μm to about 80 μm.

Clause 89. The shunt of any one of Clauses 64-75 or 85-88, wherein the removable portion comprises an axial thickness of between about 40 μm to about 50 μm.

Clause 90. The shunt of any one of Clauses 64-75 or 85-89, wherein the removable portion comprises an axial thickness of about 45 μm.

Clause 91. The shunt of any one of Clauses 64-75 or 85-87, wherein the removable portion comprises an axial thickness of 32 μm to about 1200 μm.

Clause 92. The shunt of any one of Clauses 64-75, 85-87, or 91, wherein the removable portion comprises an axial thickness of about 40 μm to about 800 μm.

Clause 93. The shunt of any one of Clauses 64-75, 85-87, or 91-92, wherein the removable portion comprises an axial thickness of about 80 μm to about 400 μm.

Clause 94. The shunt of any one of Clauses 64-75, 85-87, or 91-93, wherein the removable portion comprises an axial thickness of about 160 μm to about 240 μm.

Clause 95. A method of manufacturing the shunt of Clause 64, comprising: dipping the outflow end portion of the shunt into a layer of liquid or viscous material to permit the material to be coupled to the outflow end portion; and drying the material to form the removable portion.

Clause 96. A method of manufacturing the shunt of Clause 64, comprising: inserting a material into the outflow end portion of the shunt to form the removable portion and couple the removable portion to the outflow end portion.

Further Considerations

In some embodiments, any of the clauses herein may depend from any one of the independent clauses or any one of the dependent clauses. In one aspect, any of the clauses (e.g., dependent or independent clauses) may be combined with any other one or more clauses (e.g., dependent or independent clauses). In one aspect, a claim may include some or all of the words (e.g., steps, operations, means or components) recited in a clause, a sentence, a phrase or a paragraph. In one aspect, a claim may include some or all of the words recited in one or more clauses, sentences, phrases or paragraphs. In one aspect, some of the words in each of the clauses, sentences, phrases or paragraphs may be removed. In one aspect, additional words or elements may be added to a clause, a sentence, a phrase or a paragraph. In one aspect, the subject technology may be implemented without utilizing some of the components, elements, functions or operations described herein. In one aspect, the subject technology may be implemented utilizing additional components, elements, functions or operations.

A reference to an element in the singular is not intended to mean one and only one unless specifically so stated, but rather one or more. For example, "a" module may refer to one or more modules. An element proceeded by "a," "an," "the," or "said" does not, without further constraints, preclude the existence of additional same elements.

Headings and subheadings, if any, are used for convenience only and do not limit the invention. The word exemplary is used to mean serving as an example or illustration. To the extent that the term include, have, or the like is used, such term is intended to be inclusive in a manner similar to the term comprise as comprise is interpreted when employed as a transitional word in a claim. Relational terms such as first and second and the like may be used to distinguish one entity or action from another without necessarily requiring or implying any actual such relationship or order between such entities or actions.

Phrases such as an aspect, the aspect, another aspect, some aspects, one or more aspects, an implementation, the implementation, another implementation, some implementations, one or more implementations, an embodiment, the embodiment, another embodiment, some embodiments, one or more embodiments, a configuration, the configuration, another configuration, some configurations, one or more configurations, the subject technology, the disclosure, the present disclosure, other variations thereof and alike are for convenience and do not imply that a disclosure relating to such phrase(s) is essential to the subject technology or that such disclosure applies to all configurations of the subject technology. A disclosure relating to such phrase(s) may apply to all configurations, or one or more configurations. A disclosure relating to such phrase(s) may provide one or more examples. A phrase such as an aspect or some aspects may refer to one or more aspects and vice versa, and this applies similarly to other foregoing phrases.

A phrase "at least one of" preceding a series of items, with the terms "and" or "or" to separate any of the items, modifies the list as a whole, rather than each member of the list. The phrase "at least one of" does not require selection of at least one item; rather, the phrase allows a meaning that includes at least one of any one of the items, and/or at least one of any combination of the items, and/or at least one of each of the items. By way of example, each of the phrases "at least one of A, B, and C" or "at least one of A, B, or C" refers to only A, only B, or only C; any combination of A, B, and C; and/or at least one of each of A, B, and C.

It is understood that the specific order or hierarchy of steps, operations, or processes disclosed is an illustration of exemplary approaches. Unless explicitly stated otherwise, it is understood that the specific order or hierarchy of steps, operations, or processes may be performed in different order. Some of the steps, operations, or processes may be performed simultaneously. The accompanying method claims, if any, present elements of the various steps, operations or processes in a sample order, and are not meant to be limited to the specific order or hierarchy presented. These may be performed in serial, linearly, in parallel or in different order. It should be understood that the described instructions, operations, and systems can generally be integrated together in a single software/hardware product or packaged into multiple software/hardware products.

In one aspect, a term coupled or the like may refer to being directly coupled. In another aspect, a term coupled or the like may refer to being indirectly coupled.

Terms such as top, bottom, front, rear, side, horizontal, vertical, and the like refer to an arbitrary frame of reference, rather than to the ordinary gravitational frame of reference. Thus, such a term may extend upwardly, downwardly, diagonally, or horizontally in a gravitational frame of reference.

The disclosure is provided to enable any person skilled in the art to practice the various aspects described herein. In some instances, well-known structures and components are shown in block diagram form in order to avoid obscuring the concepts of the subject technology. The disclosure provides various examples of the subject technology, and the subject technology is not limited to these examples. Various modifications to these aspects will be readily apparent to those skilled in the art, and the principles described herein may be applied to other aspects.

All structural and functional equivalents to the elements of the various aspects described throughout the disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims. No claim element is to be construed under the provisions of 35 U.S.C. § 112, sixth paragraph, unless the element is expressly recited using the phrase "means for" or, in the case of a method claim, the element is recited using the phrase "step for."

The title, background, brief description of the drawings, abstract, and drawings are hereby incorporated into the disclosure and are provided as illustrative examples of the disclosure, not as restrictive descriptions. It is submitted with the understanding that they will not be used to limit the scope or meaning of the claims. In addition, in the detailed description, it can be seen that the description provides illustrative examples and the various features are grouped together in various implementations for the purpose of streamlining the disclosure. The method of disclosure is not to be interpreted as reflecting an intention that the claimed subject matter requires more features than are expressly recited in each claim. Rather, as the claims reflect, inventive subject matter lies in less than all features of a single disclosed configuration or operation. The claims are hereby incorporated into the detailed description, with each claim standing on its own as a separately claimed subject matter.

The claims are not intended to be limited to the aspects described herein, but are to be accorded the full scope consistent with the language claims and to encompass all legal equivalents. Notwithstanding, none of the claims are intended to embrace subject matter that fails to satisfy the requirements of the applicable patent law, nor should they be interpreted in such a way.

What is claimed is:

1. A shunt for draining fluid from an interior chamber of an eye, the shunt comprising:
   a main section having an inflow end portion, an outflow end portion, and wall defining a lumen,
   a removable portion coupled to and extending distally beyond the outflow end portion to block flow through the lumen when present to provide a first nonzero flow rate, the removable portion providing a burstable seal across the outflow end portion and, upon application of compressive force against the shunt, being configured to (i) rupture and become separated from the shunt and displaced within the eye into an outflow area that has a lower pressure than the anterior chamber, (ii) act as a spacer and maintain patency of the outflow area, and (iii) facilitate fluid to flow through the lumen from the anterior chamber toward the outflow area at a second flow rate greater than the first nonzero flow rate.

2. The shunt of claim 1, wherein the removable portion comprises a disk-shaped membrane coupled to the outflow end portion.

3. The shunt of claim 2, wherein the wall of the main section comprises a first thickness and the membrane comprises a second thickness, the first thickness being greater than the second thickness.

4. The shunt of claim 2, wherein the membrane is positioned within the lumen.

5. The shunt of claim 1, wherein the removable portion has a bulbous shape and overlaps an outer surface of the shunt adjacent to the outflow end portion.

6. The shunt of claim 1, wherein the removable portion comprises an outer cross-sectional profile greater than an outer diameter of the shunt.

7. A method of adjusting a flow rate of an intraocular shunt implanted in an eye, the method comprising:
   determining a position of the intraocular shunt in the eye extending between an anterior chamber of the eye and a location of lower pressure of the eye; and
   applying a force to an outer surface of the eye to separate the removable portion that extends distally beyond an outflow portion of the intraocular shunt and to reposition the removable portion to a location in an outflow area within the eye having a lower pressure than the anterior chamber and separated from the intraocular shunt to act as a spacer and maintaining patency of the outflow area, thereby permitting an increased flow rate through the intraocular shunt from a nonzero flow rate.

8. The method of claim 7, wherein the removable portion comprises a first inner cross-sectional dimension and the intraocular shunt comprises a second inner cross-sectional dimension greater than the first inner cross-sectional dimension, and wherein the applying a force comprises compressing the second inner cross-sectional dimension to be smaller than the first inner cross-sectional dimension.

9. The method of claim 7, wherein the applying a force comprises positioning the removable portion in a location spaced apart from an exit of the outflow portion after separating the removable portion from the intraocular shunt.

10. The method of claim 9, further comprising extracting the removable portion from the eye after separating the removable portion from the outflow portion.

11. The method of claim 7, wherein at least a portion of the removable portion is disposed internally within the intraocular shunt.

12. The method of claim 7, wherein applying a force to the outer surface of the eye comprises applying a force via a finger.

13. A method of adjusting a flow rate of an intraocular shunt implanted in an eye, the method comprising:
   determining a position of an outflow end of the intraocular shunt underlying a conjunctiva of the eye, the shunt being operative to permit flow of aqueous humor from an anterior chamber of the eye; and
   massaging the outflow end of the shunt to dislodge a plug, extending distally beyond the outflow end, lumen of the shunt and to reposition the plug to a location separated from the shunt to an outflow area within the eye having lower pressure than the anterior chamber to act as a spacer and maintaining patency of the outflow area, thereby modifying a flow rate through the shunt from a nonzero flow rate.

14. The method of claim 13, wherein the massaging the outflow end comprises positioning the plug in a location spaced apart from an exit of the outflow end after dislodging the plug from the lumen.

15. The method of claim 14, further comprising extracting the plug from the eye after dislodging the plug from the outflow end.

16. The method of claim 13, wherein the massaging the outflow end comprises massaging the conjunctiva of the eye to massage the outflow end of the intraocular shunt.

17. A shunt for treating glaucoma by draining fluid from an anterior chamber of an eye, the shunt comprising a main section and a blocking portion that is displaceably coupled to and extending distally beyond an outflow end portion of the main section, the blocking portion being configured to (1) block fluid flow therethrough in an occluding position at a nonzero flow rate and (2) to be repositioned at a flow position in which the blocking portion is separated from the main section upon application of compressive force against the shunt such that the blocking portion acts as a spacer within and maintains patency of an outflow area of the eye, thereby increasing flow through the shunt from the nonzero flow rate.

18. The shunt of claim 17, wherein the removable portion comprises a material being any of a metal and a gelatin.

19. The shunt of claim 1, wherein the removable portion comprises a material being any of a metal and a gelatin.

* * * * *